United States Patent
Mooney et al.

(10) Patent No.: US 6,642,363 B1
(45) Date of Patent: Nov. 4, 2003

(54) POLYMERS CONTAINING POLYSACCHARIDES SUCH AS ALGINATES OR MODIFIED ALGINATES

(75) Inventors: David J. Mooney, Ann Arbor, MI (US); Kamal H. Bouhadir, Ann Arbor, MI (US); Wai Kung Wong, Laguna (HK); Jon A. Rowley, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/147,900

(22) PCT Filed: Sep. 19, 1997

(86) PCT No.: PCT/US97/16890
§ 371 (c)(1),
(2), (4) Date: May 3, 1999

(87) PCT Pub. No.: WO98/12228
PCT Pub. Date: Mar. 26, 1998

Related U.S. Application Data

(60) Provisional application No. 60/041,565, filed on Mar. 21, 1997, provisional application No. 60/026,362, filed on Sep. 19, 1996, and provisional application No. 60/026,467, filed on Sep. 19, 1996.

(51) Int. Cl.⁷ .......................... C08B 37/04; C07H 1/00; A61K 38/00; A61K 31/715
(52) U.S. Cl. .............................. 536/3; 536/124; 514/2; 514/54
(58) Field of Search ...................... 536/3, 124; 514/2, 514/54

(56) References Cited

U.S. PATENT DOCUMENTS

| | | |
|---|---|---|
| 4,115,305 A | 9/1978 | Hornby et al. |
| 4,663,287 A | 5/1987 | Barker ........................ 435/188 |
| 5,110,605 A | 5/1992 | Acharya ...................... 424/487 |
| 5,144,016 A | 9/1992 | Skjak-Braek et al. .......... 536/3 |
| 5,227,298 A | 7/1993 | Weber et al. ................ 435/178 |
| 5,429,821 A | 7/1995 | Dorian et al. ............... 424/424 |
| 5,622,718 A | 4/1997 | Al-Shamkhani et al. ....... 536/3 |
| 5,705,177 A * | 1/1998 | Roufa et al. ................ 424/422 |
| 5,837,747 A * | 11/1998 | Soon-Shiong et al. ........ 522/26 |

FOREIGN PATENT DOCUMENTS

| | | |
|---|---|---|
| EP | 0 614 914 A | 9/1994 |
| EP | 0 614 914 A | 9/1994 |
| EP | 0 712 635 | 5/1996 |
| EP | 0 712 635 A | 5/1996 |
| WO | 94/17786 A | 8/1984 |
| WO | 93/09176 A | 5/1993 |
| WO | WO 93/09176 | 5/1993 |
| WO | 93/21906 A | 11/1993 |
| WO | WO 93/21906 | 11/1993 |
| WO | 94/07536 A | 4/1994 |
| WO | WO 94/07536 | 4/1994 |
| WO | WO 95/24429 | 9/1995 |
| WO | 95/24429 A | 9/1995 |

OTHER PUBLICATIONS

Knirel et al., Structure of Pseudomonas Aeruginosa Immunotype 3 O–Specific Polysaccharide; Revision of the Structure of Acetamidino Derivative of 2,3–diamino–2, 3–dideoxy Mannuronic acid', Bioorg. Khim. (1986), 127 (7), pp. 995–997.*

(List continued on next page.)

*Primary Examiner*—James O. Wilson
*Assistant Examiner*—Everett White
(74) *Attorney, Agent, or Firm*—Millen, White, Zelano & Branigan, P.C.

(57) ABSTRACT

Materials which contain polysaccharide chains, particularly alginate or modified alginate chains. The polysaccharide chains may be included as side chains or auxiliary chains from a backbone polymer chain, which may also be a polysaccharide. Further, the polysaccharide chains may be cross-linked between side chains, auxiliary chains and/or backbone chains. These materials and non-modified or otherwise modified alginate materials are advantageously modified by covalent bonding thereto of a biologically active molecule for cell adhesion or other cellular interaction. Processes for preparation of these alginate materials and methods for using them, particularly for cell transplantation and tissue engineering applications.

53 Claims, 12 Drawing Sheets-

OTHER PUBLICATIONS

Smidsrod et al., "Chemistry and Phsical Properties of Alginates", Carbohydrates In Europe, May 1996, vol. 14, pp. 6–13.*

Skjak–Braek et al., "Application of Alginate Gels in Biotechnology and Biomedicine", Carbohydrates In Europe, May 1996, vol. 14, pp. 19–25.*

Dumitriu et al., "Hydrogels Based on Polysaccharides". Polysaccharides In Medicinal Applications. Edited by Severian Dumitriu. New York: Marcel Dekker, Inc., 1996, pp. 144–207.*

Hermanson. Bioconjugate Techniques. San Diego. Academic Press, Inc.. 1996, pp. xii–xix.*

T. Matsuda et al., "Ceric–Ion–Initiating Surface Graft Polymerization With Regional Control and Dimensional Precision", Macromolecules, vol. 29, Nov. 4, 1996, pp. 7446–7451.

* cited by examiner

Linear polymers

Branched polymers

Dentritic polymers

Comb polymers

Cross-linked polymers

— Polymer backbone
O  Linker
∼ Carbohydrate chain

POLYMERS CONTAINING POLYSACCHARIDES SUCH AS ALGINATES OR MODIFIED ALGINATES

Priority is claimed to the following U.S. provisional applications: Ser. No. 60/026,362 filed Sep. 19, 1996; Ser. No. 60/026,467 filed Sep. 19, 1996; and Ser. No. 60/041,565 filed Mar. 21, 1997.

This application is a 371 of PCT/US97/16890, filed Sep. 19, 1997.

The invention relates to materials which contain polysaccharide chains, particularly alginate or modified alginate chains. The polysaccharide, particularly alginate or modified alginate, chains may be included as side chains or auxiliary chains from a backbone polymer chain, which may also be a polysaccharide. Further, the polysaccharide chains may be crosslinked between side chains, auxiliary chains and/or backbone chains. These materials are advantageously modified by covalent bonding thereto of a biologically active molecule for cell adhesion or other cellular interaction. The materials are particularly useful to provide polymeric matrices for many applications, such as in tissue engineering applications for bone or soft tissue replacement. For example, the loss of bony tissue is a central feature of many aspects of clinical dentistry (e.g. periodontal disease, caries, osteotomy for repair of trauma) and matrices from the materials described herein can be useful for repair or replenishment of lost bony tissue. The materials are also useful for drug delivery applications when the biologically active molecule is attached by a degradeable bond.

Unmodified alginate, a polysaccharide, has been previously utilized as a tissue engineering matrix in cell encapsulation and transplantation studies. It provides a useful matrix because cells can be immobilized within alginate with little cell trauma and alginate/cell mixtures can be transplanted in a minimally invasive manner. However, cells exhibit little or no adhesion or interaction with unmodified alginate. One aspect of this invention is to provide a matrix which combines specific cell adhesion ligands in the matrix such that high control over cell-matrix interactions, due to cell adhesion and matrix interactions, is attained.

One embodiment of the invention is directed to polymers containing a polymer backbone to which is linked polysaccharide groups, particularly of alginates or modified alginates, which preferably are polymerized D-mannuronate and/or L-guluronate monomers. The polysaccharide, particularly alginate, groups are present as side chains on the polymer backbone which is intended to include side chains at the terminal end of the backbone, thus being a continuation of the main chain. The polymers provide synthetic modified polysaccharides and alginates exhibiting controllable properties depending upon the ultimate use thereof. Further, the invention is directed to processes for preparing such polymers and to the use of such polymers, for example, as cell transplantation matrices, preformed hydrogels for cell transplantation, non-degradable matrices for immunoisolated cell transplantation, vehicles for drug delivery, wound dressings and replacements for industrially applied alginates.

Another embodiment of the invention is directed to polysaccharides, particularly alginates, which are modified by being crosslinked. The alginates may further be modified by covalent bonding thereto of a biologically active molecule for cell adhesion or other cellular interaction. Crosslinking of the alginate can particularly provide aloinate materials with controlled mechanical properties and shape memory properties which greatly expand their range of use, for example, to tissue engineering applications where size and shape of the matrix is of importance. The modification of the crosslinked alginates with the biologically active molecules can provide a further three-dimensional environment which is particularly advantageous for cell adhesion, thus making such alginates further useful as cell transplantation matrices. Further, the invention is directed to processes for preparing such crosslinked alginates and to their use, for example, for forming materials for tissue engineering and/or having cell adhesion properties particularly for cell transplantation matrices, such as injectable cell transplantation solutions and preformed materials for cell transplantation.

Another embodiment of the invention is directed to modified alginates, such as alginate backbone (i.e. unmodified alginate) or the above described side chain alginates or crosslinked alginates, modified by covalent bonding thereto of a biologically active molecule for cell adhesion or other cellular interaction, which is particularly advantageous for maintenance, viability and directed expression of desirable patterns of gene expression. The modified alginate polymers provide a three-dimensional environment which is particularly advantageous for cell adhesion. Further, the invention is directed to processes for preparing such polymers and to the use of such polymers, for example, for forming gels or highly viscous liquids having cell adhesion properties particularly for cell transplantation matrices, such as injectable cell transplantation solutions and preformed hydrogels for cell transplantation.

Further aspects of the invention may be determined by one of ordinary skill in the art from the following description.

BACKGROUND OF THE INVENTION

Organ or tissue failure remains a frequent, costly, and serious problem in health care despite advances in medical technology. Available treatments now include transplantation of organs from one individual to another, performing surgical reconstructing, use of mechanical devices (e.g., kidney dialyzer) and drug therapy. However, these treatments are not perfect solutions. Transplantation of organs is limited by the lack of organ donors, possible rejection and other complications. Mechanical devices cannot perform all functions of an organ, e.g., kidney dialysis can only help remove some metabolic wastes from the body. Likewise, drug levels comparable to the control systems of the body is difficult to achieve. This is partially due to difficulties in controlling the drug level in vivo. Financially, the cost of surgical procedures is very high. Advances in medical, biological and physical sciences have enabled the emergency of the field of tissue engineering. "Tissue engineering" is the application of the principles and methods of engineering and the life sciences toward the fundamental understanding of structure/function relationships in normal and pathological mammalian tissues and the development of biological substitutes to restore, maintain or improve function. It thus involves the development of methods to build biological substitutes as supplements or alternatives to whole organ or tissue transplantation . The use of living cells and/or extracellular matrix (ECM) components in the development of implantable parts or devices is an attractive approach to restore or to replace function. The advantage of this approach over whole organ/tissue transplantation is that only the cells of interest are implanted, and they potentially can be multiplied in vitro. Thus, a small biopsy can be grown into a large tissue mass and, potentially, could be used to treat many patients. The increased tissue supply may reduce the cost of the therapy because early intervention is possible during the disease, and this may prevent the long-term hospitalization which results as tissue failure progresses. The use of immunosuppression may also be avoided in some applications by using the patient's own cells.

Alginate is a linear polysaccharide, isolated, for example, from brown sea algae, which forms a stable hydrogel in the presence of divalent cations (e.g., $Ba^{++}$, $Ca^{++}$) (Smidsrod et al (1990): Alginate as immobilization matrix for cells. *TIBTECH*, 8:71–78.) Alginate is currently being used for the in vitro culture of some cells types, as an injectable cell delivery matrix, for immunoisolation based therapies, and as an enzyme immobilization substrate (Atala et al., 1993: Injectable alginate seeded with chondrocytes as a potential treatment for vesicoureteral reflux. *J. Urology*, 150:745:747; Levesque et al., 1992: Maintenance of long-term secretory function by microencapsulated islets of Langerhans. *Endocrinology*, 130:644–650; Dominguez et al., 1988: Carbodiimide coupling of $\mu$-galactosidase from *Aspergillus oryzae* to alginate. *Enzyme Microb. Technol.*, 10:606–610; and Lee et al. 1993: Covalent Immobilization of Aminoacylase to Alginate for L-hphenylalanine production. *J. Chem. Tech. Biotechnol*, 58:65–70.). Alginate hydrogels are attractive for use with cells because of their mild gelling conditions, low diffusional barriers to cell nutrients, and low inflammatory and nontoxicity in vivo (Smidsrod, supra).

Alginates occur naturally as copolymers of D-mannuronate (M) and L-guluronate (G) and have different monomer compositions when isolated from different natural sources. The block length of monomer units, overall composition and molecular weight of the alginate influence its properties. For example, calcium alginates rich in G are stiff materials, (see Sutherland, I W (1991): Alginates. In *Biomaterials.: Novel materials from biological sources.*). It is theorized that gel formation is due primarily to the G-block, and that the M-block is essentially non-selective. In such arrangement, the calcium ions would be selectively bound between sequences of polyguluronate residues and held between diaxially linked L-guluronate residues which are in the $^1C_4$ chair conformation. The calcium ions would thus be packed into the interstices between polyguluronate chains associated pairwise and this structure is named the "egg-box" sequence. The ability to form a junction zone depends on the length of the G-blocks in different alginates (Sutherland, supra.). Other advantages of alginates include their wide availability, low diffusional barrier for all nutrients and relative biocompatibility (Smidsrod et al., Trends in Biotech, 8:71–78, 1990).

A limitation of alginate hydrogels used with a cellular component is the lack of inherent cell adhesion. Such is necessary for cell attachment and long term survival of most mammalian cell systems. While chrondrocytes and islets of Langerhans have been successfully transplanted using alginates, the absence of suitable cell adhesion by alginates practically limits their use to cartilage and islet cell applications. Most other cell types require attachment to an extracellular substrate to remain viable.

Previous attempts have been made to create a three-dimensional hydrogel environment incorporating cell adhesion ligands for cell attachment and survival. One system is a photopolymerizable polyacrylamide based hydrogel with an RGD peptide grafted onto the polymer backbone. This polymer undergoes photogelation in the presence of UV light, and may be polymerized as a polymer/cell hybrid (Moghaddam et al., 1993: Molecular design of three-dimensional artificial extracellular matrix: photosensitive polymers containing cell adhesive peptide. *J. Polymer Science: Part A: Polymer Chem.* 31:1589–1597.) Another is a polyacrylamide system, again with the RGD ligand covalently attached, which is catalytically polymerized prior to any biological interactions (Woerly et al. 1995: Intracerebral implantation of hydrogel-coupled adhesion peptides: tissue reaction. *J. Neural Transplant. Plasticity*, 5:245:255.). A disadvantage of such systems is that conversion of the polymers from a liquid to a solid, gel or highly viscous system requires conditions which are detrimental to cell viability, e.g., use of organic solvents and/or elevated temperatures.

Another major limitation of alginate hydrogels used in biotechnology applications is that their stability is dependent solely on calcium (or other divalent cation) binding, and this can present a limitation in the use of these materials (e.g., loss of calcium from gels leads to gel dissolution). In addition, alginate hydrogels have a limited range of physical properties due to the limited number of variables one can currently manipulate (i.e., alginate concentration, specific divalent cation used for gelling, and concentration of divalent cation). This limitation is especially evident when alginate is utilized as an injectable cell delivery vehicle in tissue engineering. It is not possible to obtain a pre-defined and desirable shape of the matrix following injection, and it is thus not possible to create a new tissue with a specific and desirable shape and size. This is especially important whenever the size and shape of the new tissue are critical to the function of the tissue, for example, in reconstruction of facial features such as nose or ears, or relining of joints.

SUMMARY OF THE INVENTION

An object of the present invention was to design improved synthetic analogues of alginates, to provide a process for preparing such polymers and to provide compositions and methods utilizing such polymers, particularly in tissue engineering applications. It is further useful according to the invention to provide alginate-containing materials in which the gel stability is related to an additional variable besides cation binding from the divalent cations. Thus, for example, the disadvantages of the previous systems can be avoided by providing an alginate which can be gelled or made highly viscous under mild conditions, i.e., in the presence of divalent metal cations such as $Ca^{++}$ or $Ba^{++}$ in aqueous systems, without requiring, for example, organic solvents and/or increased temperature.

In one embodiment, the invention provides polymers with side chains of polysaccharides in general which may not exhibit the gelling behavior of alginates, but which provide polysaccharides with controllable properties, such as degradation. These polymers may comprise a polymeric backbone section to which is covalently linked a polysaccharide side chain. Another embodiment provides a polymeric backbone section to which is bonded a side chain, preferably multiple side chains, of polymerized, optionally modified, D-mannuronate (M units) and/or L-guluronate (G units) monomers. The modified alginates preferably maintain the mild gelling behavior of conventional alginates, but do not have the disadvantages discussed above. The linkage between the polymeric backbone section and the side chain (s) may be provided by difunctional or multifunctional linker compounds, by groups incorporated within the polymeric backbone section reactive with the polysaccharide units and/or by groups on the polysaccharide units or derivatives thereof reactive with groups on the polymeric backbone section. The polymers may advantageously further comprise biologically active molecules bonded thereto, particularly preferably bonded through the carboxylic acid groups on M and/or G units. In a particularly preferred embodiment, the side chains are alginates, the biologically active molecules exhibit cell adhesion properties and the polymers are useful for cell transplantation.

An advantageous aspect of these materials is the ability to provide a polymer analogous to alginates, but with high controllability of the properties, particularly when used for cell transplantation purposes. The chemical structures, functionality and sizes of the different parts of the polymer, i.e., the backbone, linker, side chain and, optionally, biologically active molecule(s) can be provided so as to control many properties of the polymer in physiological systems, such as, for example, degradeability, biocompatibility, organ or tissue specificity and affinity, cell adhesion, cell growth and cell differentiation, manner and rate of removal from the system, solubility and viscosity.

As the polymeric backbone section there can be used any homo- or co-polymer which is compatible with the ultimate use and which has the appropriate functional groups such that it can be covalently linked directly or through a linker to the polysaccharide, particularly polymerized M and/or G units, or suitable modifications thereof. Any polymer meeting the above requirements is useful herein, and the selection of the specific polymer and acquisitions or preparation of such polymer would be conventionally practiced in the art. See *The Biomedical Engineering Handbook*, ed. Bronzino, Section 4, ed. Park. Preferred for such polymeric backbone section are, for example, poly(vinyl alcohols), poly(alkylene oxides) particularly poly(ethylene oxides), polypeptides, poly(amino acids), such as poly(lysine), poly(allylamines) (PAM), poly(acrylates), modified styrene polymers such as poly(4-aminomethylstyrene), polyesters, polyphosphazenes, pluronic polyols, polyoxamers, poly(uronic acids) and copolymers, including graft polymers thereof.

The polymeric backbone section may be selected to have a wide range of molecular weights, generally from as low as 100 up to ten million. However, by selection of the molecular weight and structure of the polymeric backbone section the occurrence and rate of degradeability of the polymer and the manner and rate of release from physiological systems of the polymer can be influenced. For instance, a high molecular weight non-degradable polymeric backbone section, for instance having a molecular weight above about 100,000, will in general provide a more stable polymer which may be useful in, for example, nondegradable matrices for immunoisolated cell transplantation. Alternatively, a polymeric backbone section having a molecular weight of less than about 30,000 to 50,000 or one in which the backbone itself is degradable can be cleared through the kidneys and by other normal metabolic routes. Polymers with a degradable polymeric backbone section include those with a backbone having hydrolyzable groups therein, such as polymers containing ester groups in the backbone, for example, aliphatic polyesters of the poly(a-hydroxy acids) including poly(glycolic acid) and poly(lactic acid). When the backbone is itself degradable, it need not be of low molecular weight to provide such degradeability. A particular example of a degradable polymer for the backbone is a graft polymer of PEO (polyethylene oxide) and acetyl-aspartate shown by the following equation, wherein the first equation shows formation of the degradable polymer backbone, and the second schematic shows the attachment of side chains thereto:

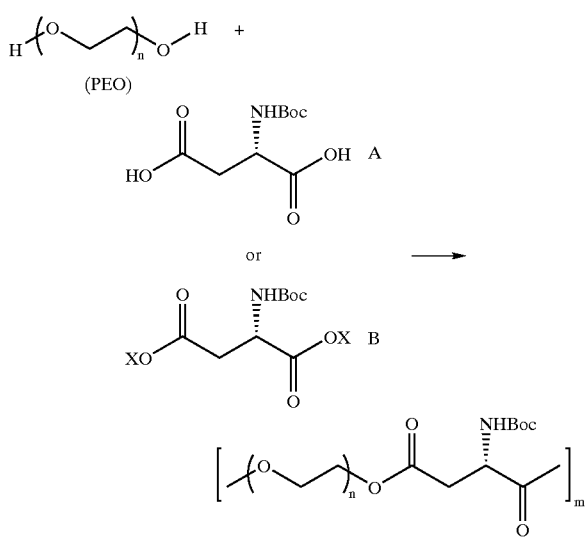

A: DCC, HOBT, DMAP, DMF, B; X=OBT or OSu, NMM, DMF.

Copolymer content can be controlled by the block length of PEO and mixing in Ac-aspartate.

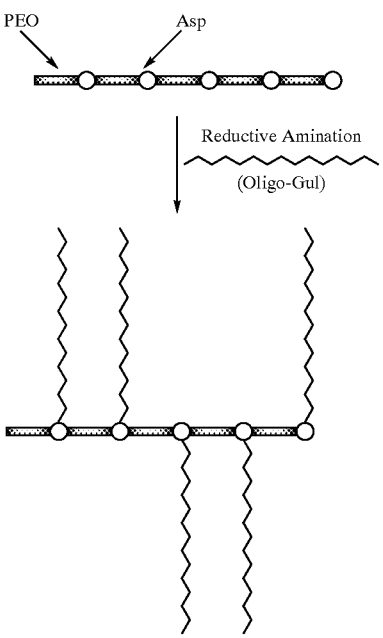

The solubility, viscosity, biocompatibility, etc., of the polymeric backbone section also is a consideration as to its effect on the desired properties of the final polymer product.

In one embodiment the polymeric backbone section can be one which incorporates linkage sites for the polysaccharide side chains so that a separate linker group is not required. For example, poly(amino acids) having free amino groups may be used for this purpose.

When a linker group is used, such linker group may be selected from any divalent moieties which are compatible with the ultimate use of the polymer and which provide for covalent bonding between the polymeric backbone section and the polysaccharide side chain(s). Such linker groups are conventionally known in the art for such purpose, and can be linked to the backbone in a conventional manner. For linking of the linker or linkage site on the polymer to the polysaccharide, since the polysaccharide is generally bonded through a carboxylate group, chemistries useful for reacting with carboxylate groups are particularly useful in providing the linker or linkage site on the polymer; see Bronzino and Hermanson, cited below. The linker group may be selected to significantly affect the biodegradability of the polymer depending upon the extent of hydrolyzability of groups in the linker chain. Amino acid linkers and derivatives thereof are preferred due to the controllability of the degradation feature. For example, amino acid linker groups, such as glycine, will provide ester linkages which are readily hydrolyzable and, thus, facilitate degradation of the polymer in an aqueous environment, whereas, amino alcohols provide an ether linkage which is significantly less degradable. Amino aldehydes are also useful linker groups. The substituent groups on the amino acids will also affect the rate of degradeability of the linkage. The linker group may also be varied in chain length depending upon the desired properties. Linkages providing, for example, from 1 to 10 atoms between the backbone and side chain, are preferred, although longer linkage chains are possible. Further, the linker may be branched to provide multiple attachment sites for the side chains, for example, to provide a dendrite configuration such as shown in Example 5. The linker will be in the form of a residue of the linking compound without the group removed during bonding.

The side chains are polysaccharides, preferably optionally modified alginate units, which enable the preparation of a gel or highly viscous liquid in the presence of a divalent metal, e.g., $Ca^{++}$or $Ba^{++}$. Preferably they are comprised of polymerized D-mannuronate (M) and/or L-guluronate (G) monomers, but, also encompass modified such monomers. The side chains are particularly preferably comprised of oligomeric blocks of M units, G units or M and G units. The molecular weight of each side chain or the number of units and length of such side chains is again a function of the desired ultimate properties of the polymer and selectability of this aspect is an advantageous feature of the invention. Although there is no specific limitation, the molecular weight of the side chain may range from about 200 up to one million, and may contain, preferably 2 to 5,000 M and/or G units. As with the polymeric backbone section, higher molecular weight side chains, e.g. above about 100,000, are generally useful when more stable polymers are desired and lower molecular weight side chains, e.g., below about 30,000 to 50,000, are generally useful when biodegradable species capable of removal through the kidneys, or other normal functions, are desired.

The distribution of M and G units also provides a controllability feature of the invention with a higher ratio of G units generally providing a stiffer polymer which will hold its shape better. Side chains having a percentage of G units based on the total of M & G units of from 10 to 100% are particularly preferred. Increasing or decreasing the number of G units in the side chains will also allow for increasing or decreasing the rate of gelation of the polymer. Such may be of interest when the polymers are used in injectable solutions and the rate is controlled so that the solution will gel at the appropriate time after injection. The number of side chains provided on the polymeric backbone section also will affect the extent and rate of gelation and, thus, will vary depending on the ultimate use. In general, more side chains will result in a more rigid, compact polymer, and provide a more dense concentration of attached biologically active molecules, if present. The number of side chains is preferably from 1 to 100% of the reactive monomer units available on the backbone per polymer molecule. It is not necessary that every linker group or linkage site be provided with a side chain. For example, free linkers or linkage sites may be left to facilitate the solubility and/or compatibility of the polymer in its intended system. Additionally, free linkers or linkage sites may be provided to allow for the later addition of differently structured or proportioned alginate side chains or other side chains.

Furthermore, the whole side chain or individual M and/or G units may be modified from the naturally occurring units. Naturally occurring M and G alginate units exhibit the same general chemical structure irrespective of their source, although, the distribution and proportions of M and G units will differ depending upon the source. Natural source alginates, for example from seaweed or bacteria, can thus be selected to provide side chains with appropriate M and G units for the ultimate use of the polymer. Isolation of alginate chains from natural sources for use as the side chains herein can be conducted by conventional methods. See *Biomaterials: Novel Materials from Biological Sources*, ed. Byrum, Alginates chapter (ed. Sutherland), p. 309–331 (1991). Alternatively, synthetically prepared alginates having a selected M and G unit proportion and distribution prepared by synthetic routes analogous to those known in the art can be used as the side chains. Further, either natural or synthetic source alginates may be modified to provide M and G units with a modified structure as long as the polymers with modified side chains still provide a gel or highly viscous liquid by interaction of the alginate units with a divalent metal. The M and/or G units may be modified, for example, with polyalkylene oxide units of varied molecular weight such as shown for modification of polysaccharides in Spaltro (U.S. Pat. No. 5,490,978) with other alcohols such as glycols. Modification of the side chains with such groups generally will make the polymer more soluble, which generally will result in a less viscous gel. Such modifying groups can also enhance the stability of the polymer. Further, the polymers can be modified on the side chains to provide alkali resistance, for example, as shown by U.S. Pat. No. 2,536,893.

Useful polysaccharides other than alginates include agarose and microbial polysaccharides such as those listed in Table 1:

TABLE 1

| Polymers[a] | Structure |
| --- | --- |
| Fungal | |
| Pullulan (N) | 1,4-;1,6-α-D-Glucan |
| Scleroglucan (N) | 1,3;1,6-α-D-Glucan |
| Chitin (N) | 1,4-β-D-Acetyl Glucosamine |
| Chitosan (C) | 1,4-β-D-N-Glucosamine |
| Elsinan (N) | 1,4-;1,3-α-D-Glucan |
| Bacterial | |
| Xanthan gum (A) | 1,4-β-D-Glucan with D-mannose; D-glucuronic acid as side groups |
| Curdlan (N) | 1,3-β-D-Glucan (with branching) |
| Dextran (N) | 1,6-α-D-Glucan with some 1,2;1,3-;1,4-α-linkages |
| Gellan (A) | 1,4-β-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N-neutral, A = anionic and C-cationic.

The polymeric backbone section, linkages and side chains may be provided in a number of configurations which configuration will be a factor in the controllability of the polymer properties. The configuration of the polymeric backbone section, the number and location of linkage sites and the type and number of side chains will determine the configuration. Examples of useful configurations are shown in FIG. 1 although the invention is not limited to such configurations and further configurations using the three basic structural units can be provided according to the invention. Especially preferred, however, are polymers having the branched configuration. It is noted that the "side chains" of the linear polymers are on the terminal ends of the backbone, but are still considered side chains herein. Further, the side chains may be present between sections of polymer backbone in an alternating block type configuration.

One preferred embodiment is materials wherein the backbone itself is an alginate. The side chains, for example, may be polyguluronate derived from sodium alginate. A particular example involves cross-linking polyguluronate to itself, via a hydrolytically degradable bond, utilizing a bifunctional cross-linking molecule to form a cross-linked polymer. Dendritic polymers and comb polymers, as described below can also be provided as such materials. These structures can provide a highly cross-linked polymer which would rapidly degrade to low molecular weight components and readily be cleared by the body. To achieve this goal, for example, polyaldehyde guluronate is reacted with hydrazine and sodium borohydride to afford polyhydrazino guluronate. The hydrazine groups on this alginate derived polymer are used to incorporate G-block chains via the their hemiacetal termini. This provides materials from naturally derived polysaccharides with hydrolyzable hydrazone linkages, hence, biocompatible and biodegradable. Hydrolysis of the hydrazone linkage in these materials will lead to short chain polysaccharides that can be excreted by the kidney. Further more, reduction of the hydrazone bond by borohydrides can form a chemically stable hydrazine bond that provide nondegradable materials. Thus, both biodegradable and nondegradable biomaterials can be derived from natural polysaccharides. Cells within the polymer are not damaged by the cross-linking reaction, indicating that these materials are useful for cell transplantation, for example.

Dendrimers provide a particularly interesting backbone structure since they exhibit different properties from the corresponding linear polymers due to the difference in molecular shape and structures. Dendritic molecules can be provided as a backbone with handles to branch off a large number of functional groups in a compact region. Since polypeptides are biodegradable and their degradation products (i.e., the amino acids) are non-toxic, certain polypeptides (e.g. polylysines) can be used as dendritic handles. In connection therewith, soluble polymer supports which combine the advantages of both solid phase and solution phase syntheses can be used to prepare the materials. The most typical soluble polymer supports utilized are comprised of poly(ethylene oxide) (PEO). The reasons are the hydrophilic nature of PEO and insolubility in a variety of organic solvents which is desirable for purification purposes.

A further useful backbone structure is comb polymers which contain many side chains extending from a polymer backbone. Poly(vinyl alcohol) (PVA) provides a particularly useful backbone for comb polymers. The alcohol groups of the PVA can be esterified and subjected to the above-discussed carbodiimide linkage chemistry to provide the side chain linkages.

The materials containing a polymer backbone may be prepared utilizing synthetic methods known in the art, some of which are discussed above, for example in the *Biomedical Engineering Handbook*, section 4,; see also Odian, *Principles of Polymerization*, Chapter 9, 2nd ed., (1970). For example, polymeric backbone starting materials can be used which already contain suitable linkage sites, e.g. free amino groups such as certain poly(amino acids), or the polymers can be reacted with linker compounds to provide suitable linkage sites, particularly by the reaction of suitable sites on the polymeric backbone with amino acid derivatives, optionally with the amino groups being protected. Further, some reactive sites on the backbone may be protected to prevent addition of the linker group if it is desired to keep such sites free or to subsequently provide such sites with different linker groups. This chemistry is conventional in the field of linker/polymer formation, especially involving ester, amide, ether and other covalent linkages; see, e.g., Bronzino and Hermanson, cited above. For protective groups, see, e.g., Vogel's Textbook of Practical Organic Chemistry, 5th ed. p. 550+ and 784+. After removal of the optional protecting groups on the linker, reaction with the side chain of M and/or G units is conducted, preferably through grafting by reductive amination of the reducing end of the side chain with the amino group of the linker, to produce the subject polymers. The side chains are provided as described above from natural sources or synthetically, and may have, optionally, the described modifications they may be bonded as described above, or by other conventional methods.

Another embodiment of synthetic analogues of alginate materials are those provided by covalent crosslinking of the alginate. This covalent crosslinking greatly expands the range of situations in which these materials are useful. One specific application of this modification is the development of matrices of the alginate with shape memory. The crosslinked alginate provides advantageous shape memory properties and compression resistance properties which make them particularly advantageous for use in forming cell transplantation matrices. Shape memory matrices are designed to "remember" their original dimensions and, following injection in the body in a compact form (e.g., through a syringe) or other means of placement in the body or in other locations which they may find use, resume their original size and shape. The shape memory property of the alginate is provided by crosslinking thereof. Crosslinking can also improve the compression resistance and/or other mechanical properties of the alginate. Further, a crosslinked alginate can provide a degree of cell adhesion even without use of biologically active cell adhesion ligands. Gelling by divalent cations provides another means of increasing the viscosity and degree of structure of the alginate in addition to the crosslinking. Further, the crosslinked alginate may be covalently bonded to at least one cell adhesion ligand to provide for cell adhesion and maintenance of cell viability.

It is also an object of the invention to provide a process for preparing such crosslinked alginates and to provide compositions and methods utilizing such crosslinked alginates.

The alginate used for crosslinking according to the invention are alginate chains which contain polymerized D-mannuronate (M) and/or L-guluronate (G) monomers, but the term "alginate" or "alginate chain" as used herein also is intended to encompass chains wherein such monomers are modified such as described below when they are compatible with the ultimate use and able to be crosslinked covalently. The alginate chain is particularly preferably comprised of oligomeric blocks of M units, G units, M and G units, or mixtures of such blocks. The general structure of an alginate linear copolymer of M and G units is demonstrated by the following general formula:

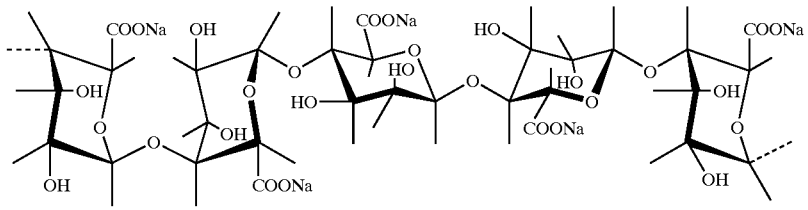

The molecular weight of the alginate chain and, thus, the number of units and length of the chains may be selected dependent upon the desired properties of the polymer. In general, the molecular weight of each chain may range from about 1,000 to one million, for example. Higher molecular weight chains, e.g., above about 100,000, are generally useful when more stable alginate polymers are desired and lower molecular weight chains, e.g., below about 30,000 to 50,000, are generally useful when biodegradable species capable of removal through the kidneys or through other normal metabolic functions are desired.

The distribution of M and G units also provides a controllability feature of the invention with a higher ratio of G units generally providing a stiffer alginate material which will hold its shape better. An alginate chain having a percentage of G units based on the total of M and G units of from 10 to 100% is particularly preferred. Increasing or decreasing the number of G units in the chain will also allow for increasing or decreasing, respectively, the rate of gelation of the alginate. Such may be of interest when the alginate is used in an injectable solution and the rate is controlled so that the solution will gel at the appropriate time after injection.

The alginate chain or individual M and/or G units may also be modified from the naturally occurring units. Sources for the naturally occurring alginates and for modified alginates are described above in relation to the alginate side chains for the polymeric backbone embodiment described above.

Furthermore, useful as the alginate starting material are materials having a polymeric backbone to which is linked alginate side chains, as described above. The crosslinking may occur between side chains of the same backbone and/or between side chains of other backbones. It is also possible to have different types of alginate-containing materials with crosslinking provided between alginate sections or chains thereof. Mixtures of any of the above alginate starting materials may also be used.

The crosslinking of the alginates is by action of a crosslinking agent to provide covalent bonding, through the crosslinking agent, from the carboxylic acid groups of the uronic acid of one alginate unit to the carboxylic acid group of the uronic acid of another alginate unit. Such crosslinking is preferably between alginate units from different alginate chains. However, crosslinking may also occur between alginate units of the same chain or, in the case where the alginates are side chains on a polymer backbone as described above, crosslinking may occur between different side chains on the same or differing polymer backbones.

The crosslinking agent may be any suitable agent with at least two functional groups which are capable of covalently bonding to the carboxylic acid groups and/or alcohol groups of the alginate or modified groups therefrom. Crosslinking agents of higher functionality may also be used. For example, polyamines such as bifunctional, trifunctional, star polymers or dendritic amines are useful and these can be made, for example, by conversion from corresponding polyols. Preferred crosslinking agents are those with at least two nitrogen-based functional groups such as, for example, diamine or dihydrazide compounds; non-limiting examples thereof being diamino alkanes, Jeffamine series compounds, adipic acid dihydrazide and putrescine. Particularly preferred as a crosslinking agent is lysine, especially an ester thereof, particularly the methyl or ethyl ester.

The crosslinking agent may also be selected to provide a more or less biodegradable or non-biodegradable bond such that the lifetime of the resulting crosslinked alginate material in its environment, e.g. in vivo, can be modified for the intended utility.

The amide bonds formed when crosslinking with an amine crosslinking agent of alginates are less susceptible to hydrolytic cleavage compared to the acetal linkages between the consecutive uronic acids units of alginates. Therefore, products crosslinked with regular diamines are of relatively low biodegradability in this series of materials, since the polysaccharide (alginate) will degrade before the linking molecules will. To improve upon the rate of biodegradation, a more labile functional group may be incorporated into the crosslinker. Bifunctional biodegradable crosslinkers may be synthesized according to well established chemical pathways. See the following schematic exemplifying preparation of a crosslinking agent with biodegradable ester linking:

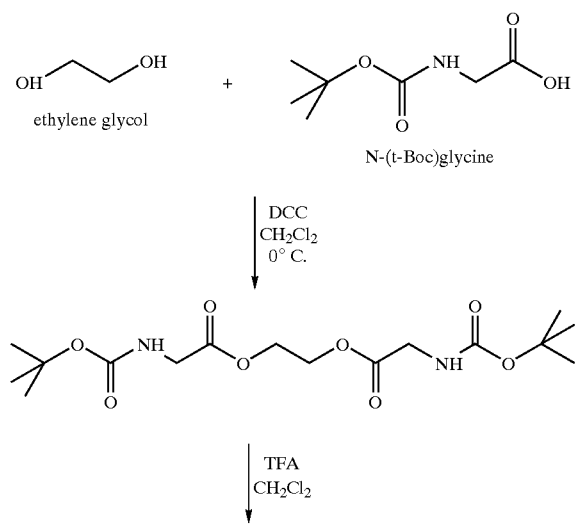

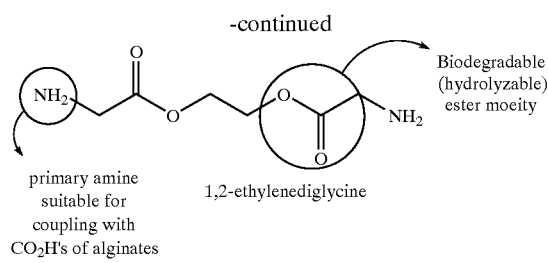

Modification of ethylene glycol to form biodegradable bifunctional crosslinkers. For example, ethylene glycol could be coupled with two N-(t-Boc)glycine using carbodiimide chemistry to yield 1,2-ethylene-(N,N'-di-t-Boc) glycine intermediate. This intermediate could be deprotected using trifluoroacetic acid in methylene chloride at various temperatures to yield 1,2-ethyleneglycoldiglycinate intermediate. This intermediate could be deprotected using trifluoroacetic acid in methylene chloride at various temperatures to yield 1,2-ethyleneglycoldiglycinate intermediate. In addition to ethylene glycol, other molecules with two terminal alcohol functional groups could be utilized. Moreover, polyols including, e.g., (star shaped or dendritic) could be transformed into similar types of crosslinkers with biodegradable ester functional groups incorporated using parallel chemical pathways.

Preferably, though not necessarily, the crosslinking is facilitated by an activator compound which reacts with the carboxylic acid group of the alginate unit to make it more reactive to the crosslinking agent. Useful activators for making a carboxylic acid group more reactive to the crosslinking agent, particularly an amine functional group of the crosslinking agent, are known in the art. Examples thereof include, but are not limited to, carbodiimides, particularly water-soluble carbodiimides such as, for example, 1-ethyl-3-(3-dimethylaminopropyl)carbodiimide (EDC), 1-cyclohexyl-3-(2-morpholinoethyl)carbodiimide (CMC), and CDI (carbodiimidazole).

Also preferred, when using an activator compound, is the use of a stabilizer for stabilizing the resulting activated group. Again, useful stabilizers for the activator groups are known in the art. For carbodiimides, particularly EDC, a useful stabilizer is 1-hydroxybenzotriazole (HOBT) which stabilizes the activated group against hydrolysis. Other useful stabilizers include N-hydroxysuccinimide and N-hydroxysulfylsuccinimide (sulfo-NHS).

The reaction sequence using a lysine ethyl ester crosslinking agent with EDC activator and HOBT stabilizer is shown in the following schematic:

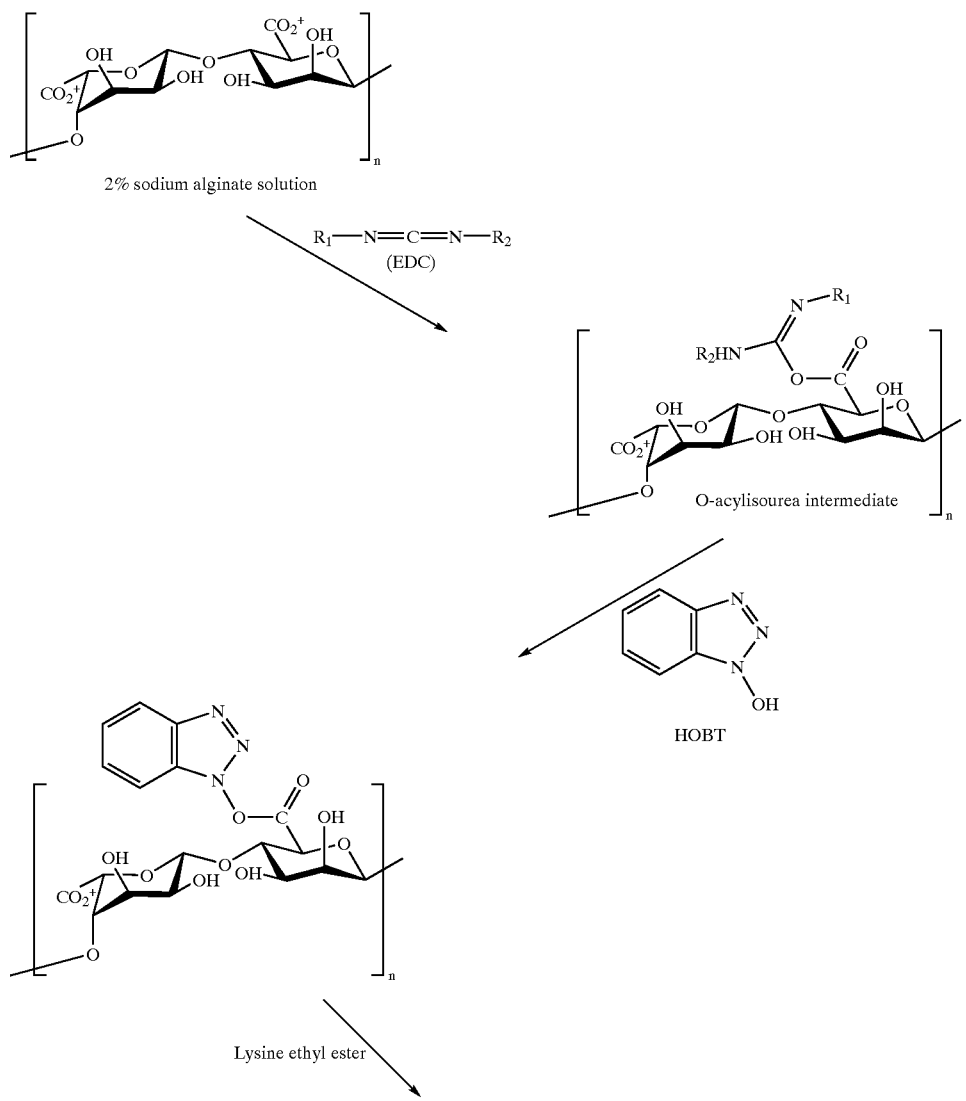

-continued

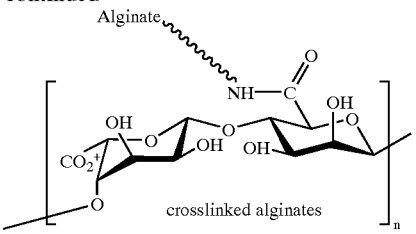
crosslinked alginates

Reaction pathway of alginate crosslinking. EDC activate carboxylic acid to yield O-acylisourea intermediate. This intermediate reacts with HOBT to form HOBT activated intermediate. Primary amino groups in lysine ethyl ester then couple the activated carboxyl groups of adjacent alginate molecules to form crosslinked alginates.

The crosslinking can generally be conducted at room temperature and neutral pH conditions, however, the conditions may be varied to optimize the particular application and crosslinking chemistry utilized. For crosslinking using the EDC chemistry, optionally with HOBT or sulfo-NHS intermediate steps, pH of from 4.0 to 8.0 and temperatures from 0° C. to room temperature (25° C.) are optimal and preferred. It is known that higher temperatures are unpreferred for this chemistry due to decomposition of EDC. Similarly, basic pH (e.g., 8–14) is also unpreferred for this reason when using this chemistry.

Other crosslinking chemistries can also be used. For example, using poly(ethylene glycol) (PEG) as a spacer in a crosslinking agent with an N-protected amino acid (see Example 12). Also, crosslinking of oxidized alginate can be conducted with adipic acid dihydrazide. The oxidation results in polyaldehyde alginates (limit oxidized alginates) for crosslinking (See Example 17). Additionally, crosslinking can be effected by light activation using photoreactive materials (See Example 26).

Another method of altering the mechanics of crosslinked systems is by varying the molecular weight between crosslinks, $M_c$, in the polymer network (Peppas and Bar-Howell, *Hydrogels in Medicine and Pharmacy*. Vol 1, CRC, Boca Raton, pp 28–55, 1986; and, Anseth et al., *Biomaterials* 17:1647–1657, 1996). $M_c$ may be modified by controlling the extent of cross-linking, or by varying the molecular weight of the cross-linking molecule (Simon et al., *Polymer* 32:2577–2587, 1991). Both of these strategies may be utilized to alter the mechanical properties of the alginate gels. Covalent cross-linking has been achieved with several different approaches. Cross-linking with lysine results in amide bond formation, which will provide stability and will degrade very slowly. PEG-crosslinkers contain an ester bond, which will be more labile to hydrolysis. Finally, cross-linking of oxidized alginate with adipic acid dihydrazide leads to a hydrazone bond. Importantly, these materials may be both covalently and ionically (e.g., calcium) cross-linked. This may prove advantageous in certain applications in which one desires a two-stage gelling. For example, the polyaldehyde alginates described below will cross-link ionically very quickly (e.g., minutes), while the covalent cross-linking reaction can be designed to occur very slowly (e.g., hours). A surgeon could thus ionically cross-link these polymers to yield a solution which is amenable to injection via a syringe or endoscope, but is viscous enough (viscosity at this stage decreases with increasing extent of oxidation) so that it does not extravasate after being placed. The covalent cross-linking would subsequently harden the implanted material into a more rigid, non-flowable mass.

Crosslinking of the alginate provides a more structured material, the extent of structuring being dependent, at least in part, on the extent of crosslinking. The extent of structuring of the alginate material will also depend, among other factors, upon the extent of gelling through action of the ionic bonding of the divalent metal cation, as discussed above, and upon the nature of the starting alginate material, which as discussed above may be varied, for example, to affect stiffness of the material. Depending on the extent of crosslinking and these other factors, the crosslinked alginate material may run the spectrum through the following forms: a viscous liquid, a swellable gel, a non-swellable gel, a swollen polymer network or a solid matrix, for example.

The extent of crosslinking is a function of the amount of crosslinking agent and crosslinking method used, i.e., the molar percent of crosslinking agent per mole of crosslinkable alginate carboxylic acid groups. The alginate will be increased in viscosity as it is crosslinked. Thus, the extent of crosslinking will be dependent upon the ultimate use. For example, to provide gel materials which have super absorbency properties, it is useful to have a low crosslinking extent, for example, of about 1 to 20%, preferably 1–10%, of crosslinkable groups crosslinked. For tissue matrix materials, for example, the extent of crosslinking is preferably from about 5% to 75%. In a particular embodiment described in the following examples, the alginate is a viscous liquid when the crosslinking agent amount is about 25 mol % or less, a swellable gel when the amount is about 50% and a solid structure which maintains its size and shape when the amount is about 75% or higher. However, the crosslinking chemistry can be selected and optimized to control viscosity even at lower crosslinking extent. In another embodiment, the crosslinking agent is used in a molar amount about equal (i.e., 100 mol %) to the number of crosslinkable alginate carboxylic acid (uronic acid) groups.

Additionally, the crosslinking can be conducted either before, after or simultaneously with the gelling by action of the divalent metal cations. It is preferred for certain applications that the crosslinking be conducted either before or simultaneously with the gelling by divalent cation so as to prevent problems with diffusion of the crosslinking agent to interior portions of the gelled material.

This material may make an ideal two-stage gelling matrix. The extent of oxidation of the alginate in the first step of the synthesis controls the binding sites available for ionic gelling, and thus regulates the viscosity of calcium cross-linked gels. The covalent cross-linking reaction with adipic acid dihydrazide occurs over several hours, and thus can be used to harden the gel slowly. The ultimate mechanical properties of the matrix can be controlled by varying the extent of covalent cross-linking, and this will be a function of the adipic acid concentration. For example, a material largely insensitive to the time of ionic cross-linking time, and with a time frame for ionic cross-linking considerably shorter than that for covalent cross-linking can be designed.

In a further embodiment, the crosslinked alginate is not gelled by action of divalent metal cations at all or is gelled by cations present in vivo only after the delivery of the crosslinked alginate into the biological system, e.g., body.

For the reasons discussed above, the extent of stiffness and matrix structure of the crosslinked alginate materials will be influenced both by the gelling by divalent cation and by the extent and nature of crosslinking. The ability to vary these and other factors provides great flexibility in designing a material which is particularly suited for its ultimate application.

In addition to the type of cell adhesion discussed below, the matrix structure provided by the crosslinked alginates themselves can facilitate cell adhesion type properties, for example, due to trapping of cells in the matrix or action of a crosslinking agent, such as lysine. For example, the crosslinked alginate as a matrix can be introduced for tissue engineering and the cell can migrate into the pores of the matrix in vivo. It is also advantageous, however, to provide the crosslinked alginates with biologically active molecules to facilitate cell adhesion or other biological interaction, as discussed below. The ligands may be added before, during or after crosslinking of the alginate and/or gelling by divalent cations.

To address the relative biological inertness of the synthetically modified polysaccharide or alginate materials discussed above, the polymers can be modified with biologically active molecules. Another aspect of the invention lies in modifying not only the above-discussed synthetic alginate analogues but also the base naturally occurring, modified or analogous alginate materials which are described herein. Even if the alginate or modified alginate material is not provided on a polymeric backbone and/or not crosslinked, the coupling of the alginate with certain biologically active molecules makes it very useful for tissue engineering and other applications.

The polymeric backbone-containing and/or crosslinked alginates and the naturally occurring or modified base alginate materials can be modified with the cell adhesion active molecule(s), for example, by covalent bonding using amide chemistry between the amine groups of the biological molecules and a free carboxylic acid group of the uronic acid residues (of M and G units) of the alginate or other polysaccharide. If the material is crosslinked, bonded to a polymeric backbone and/or otherwise modified, free acid groups must remain to add cell adhesion groups. If the cell adhesion groups are added first, active groups for any subsequent crosslinking, polymer bonding or other modification must remain. Other chemistries can also be used to effect such bonding to the biologically active molecule. For example, alginate or analogous materials can be modified to provide aldehyde groups thereon, which are reactive with the amino terminal of peptides to provide an imine bond which is reduced to a stable amine bond. An example of this chemistry is described in Example 24 herein.

Examples of suitable cell adhesion molecules include known cell attachment peptides, proteoglycan attachment peptide sequences (see Table 2), biologically active proteoglycans (e.g. laminin and fibronectin) and other polysaccharides (e.g., hyaluronic acid and chondroitin-6-sulfate). Examples of other suitable biological molecules include peptide growth factors (such as EGF, VEGF, b-FGF, acidic FGF, platelet-derived growth factor, TGF or TGF-β), and enzymes (Dominguez et al., 1988: Carbodiimide coupling of β-galactosidase from *Aspergillus oryzae* to alginate. *Enzyme Microb. Technol.*, 10:606–610; and Lee et al, 1993: Covalent Immobilization of Aminoacylase to Alginate for L-h\phenylalanine production. *J. Chem. Tech. Biotechnol*, 58:65–70). Examples of these molecules and their function are shown in the following Table 1.

TABLE 1

Proteins specific for cell binding from extracellular matrix. From Hubbell, JA (1995): Biomaterials in tissue engineering. Bio/Technology 13:565–576. One-letter abbreviations of amino acids are used, X stands for any amino acid.

| Protein | Sequence | Role |
|---|---|---|
| Fibronectin | RGDS | Adhesion of most cells, via $\alpha,\beta_1$ |
|  | LDV | Adhesion |
|  | REDV | Adhesion |
| Vitronectin | RGDV | Adhesion of most cells, via $\alpha,\beta_1$ |
| Laminin A | LRGDN | Adhesion |
|  | IKVAV | Neurite extension |
| Laminin B1 | YIGSR | Adhesion of many cells, via 67 kD laminin receptor |
|  | PDSGR | Adhesion |
| Laminin B2 | RNIAEIIKDA | Neurite extension |
| Collagen 1 | RGDT | Adhesion of most cells |
|  | DGEA | Adhesion of platelets, other cells |
| Thrombospondin | RGD | Adhesion of most cells |
|  | VTXG | Adhesion of platelets |

TABLE 2

Amino acid sequences specific for proteoglycan binding from extracellular matrix proteins. From Hubbell, above.

| PROTEIN | SEQUENCE |
|---|---|
| XBBXBX* | Consensus sequence |
| PRRARV | Fibronectin |
| YEKPGSPPREVVPRPRPGV | Fibronectin |
| RPSLAKKQRFRHRNRKGYRSQRGHSRGR | Vitronectin |
| RIQNLLKITNLRIKFVK | Laminin |

Particularly preferred as the cell adhesion molecule bonded to the alginate chain are synthetic peptides containing the amino acid sequence arginine-glycine-aspartic acid (RGD) which is known as a cell attachment ligand and found in various natural extracellular matrix molecules. Further of interest is GREDVY (endothelial cell specific) peptide. The alginates with such a modification provide cell adhesion properties to the alginate analogue, natural alginate or modified alginate, particularly when used as a cell transplantation matrix, and sustains long-term survival of mammalian cell systems, as well as controlling cell growth and differentiation.

Coupling of the cell adhesion molecules to the alginate can be conducted utilizing synthetic methods which are in general known to one of ordinary skill in the art. A particularly useful method is by formation of an amide bond between the carboxylic acid groups on the alginate chain and amine groups on the cell adhesion molecule. Other useful bonding chemistries include those discussed in Hermanson, *Bioconjugate Techniques*, p. 152–185 (1996), particularly by use of carbodiimide couplers, DCC and DIC (Woodward's Reagent K). Since many of the cell adhesion molecules are peptides, they contain a terminal amine group for such bonding. The amide bond formation is preferably catalyzed by 1-ethyl-3-(3-dimethylaminopropyl) carbodiimide (EDC), which is a water soluble enzyme commonly used in peptide synthesis. An example of such chemistry is shown in the following equation.

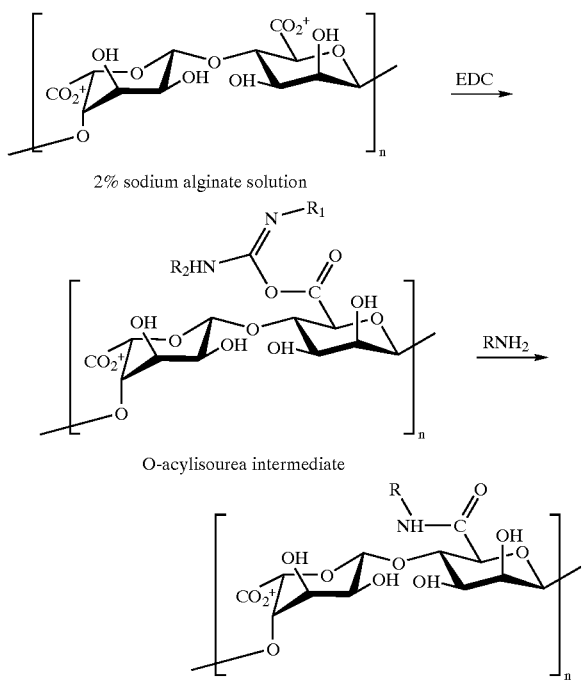

Therein, EDC reacts with carboxylate moieties on the alginate backbone creating activated esters which are reactive towards amines. R-$NH_2$ represents any molecule with a free amine (i.e. lysine or any peptide sequence N-terminus). To reduce unfavorable side reactions, EDC may be used in conjunction with N-hydroxysuccinimide, N-hydroxysulfylsuccinimide or HOBT to facilitate amide bonding over competing reactions.

The reaction conditions for this coupling chemistry can be optimized, for example, by variation of the reaction buffer, pH, EDC:uronic acid ratio, to achieve efficiencies of peptide incorporation between 65 and 75%, for example. Preferably, the pH is about 6.5 to 7.5. The ionic concentration providing the buffer (e.g. from NaCl) is preferably about 0.1 to 0.6 molar. The EDC:uronic acid groups molar ratio is preferably from 1:50 to 20:50. When HOBT is used, the preferred molar ratio of EDC:HOBt:uronic acid is about 4:1:4. The density of cell adhesion ligands, a critical regulator of cellular phenotype following adhesion to a biomaterial. (Massia and Hubbell, *J. Cell Biol*. 114:1089–1100, 1991; Mooney et al., *J. Cell Phys*. 151:497–505, 1992; and Hansen et al., *Mol. Biol. Cell* 5:967–975, 1994) can be readily varied over a 5-order of magnitude density range. An example thereof is shown in FIG. 2.

Both surface coupling, as well as bulk coupling of alginate can be readily obtained with this coupling chemistry. Therefore, by manipulation of surface and bulk coupling, materials having one type of molecule coupled internally in the matrix and another type of molecule coupled on the surface can be provided, for example.

Other methods conventionally known for attachment or immobilization of adhesion ligands may be used, such as discussed in Bronzino cited above, p. 1583–1596.

The biological molecules useful for attachment to the above-described alginate materials are not, however, limited to those providing cell adhesion function. For example, the polymer could be bound to a molecule with antiseptic function when used as a wound dressing, or which provides adhesion tissue specific gene expression, growth factors to enhance proliferation of cells in the environment or vascularation of the tissue or anti-inflammatory activity.

The combination of the alginate and alginate analogue materials with cell adhesion ligands bonded thereto provides a unique three dimensional environment in which the cells interact through various forces for adhesion to the alginate which has many uses, particularly for tissue engineering applications. The cell adhesion ligands provide specific cell membrane receptor sites for the desired cells. The number, type and location of the cell adhesion ligands on the alginate or alginate analogue material will affect the cell adhesion and cell viability maintenance properties and such factors can be varied to suit the particular application. Such applications include tissue engineering methods applied to humans and animals. Preferably, $10^{-12}$ to $10^{-4}$ moles of adhesion molecules per milliliter of hydrated alginate are used; see Massia et al., *J. Cell. Biol*; Vol. 114, p. 1089–1100 (1991). Also, combinations of the cell adhesion ligands with differing cell adhesion ligands or other bioactive molecules may be utilized according to the invention. Such additional groups may be bonded at other sites on the alginate or to suitable sites on ligands already present on the alginate or alginate analogue material.

The alginate having a polymeric backbone and/or being crosslinked or the natural or modified alginate or other polysaccharide, optionally with bioactive molecules, can create a synthetic extracellular envirornent for mammalian cells that is capable of performing the diverse functions of the natural extracellular matrix (ECM). The materials described herein will, thus, have application in the field of tissue engineering, biomaterials, and in the basic cell biological sciences for studying three dimensional cell interactions and tissue morphogenesis. The materials described herein are advantageous as a model system for creating a synthetic ECM capable of guiding cellular gene expression during in vitro or in vivo tissue formation.

The natural ECM regulates cell growth and differentiation with features that allow the control of the mechanical and chemical environment around the cells (D. E. Ingber. Mechanochemical Switching between growth and Differentiation ba, Extracellular Matrix, in Principles of Tissue Engineering (Ed, Lanza, Langer and Chick) p. 89–100 (1997)). The alginate and analogue materials are capable of displaying a wide range of mechanical properties and, with covalent modification by the bioactive molecules as described, can display a wide range of biochemical properties, such as connecting mammnalians cell with the extracellular environment which previous cell encapsulation matrices have not been capable of. The covalent modification with bioactive sequences allows the creation of a two-dimensional or three dimensional synthetic extracellular environment capable of providing biochemical signaling in the form of sequestered growth factors, hormones or active sequences within these specific chemicals, and more importantly it will allow mammalian cells to communicate with other cells directly through the alginate material via cell attachment peptides (e.g., RGD, YIGSR, REDV) covalently attached directly to the material. By then controlling the mechanical properties of the alginate material—for example by the nature of the polymer backbone and/or by crosslinking and/or by modifications of the alginate chain thereof in the manners discussed above—it will be possible to control the intercellular signaling between the cells and among cell populations (see D. E. Ingber, Mechanochemical Switching between Growth and Differentiation by Extracellular Matrix, in Principles of Tissue Engineering (Ed. Lanza, Langer and Chick )p. 89–100 (1997) and G F Oster, J D Murray, and A K Harris, Mechanical aspects of Mesenchymal Morphogenesis, Journal of Embryology and Experimental Morphology, Vol. 78, p. 83–125 (1983)).

Unmodified alginate has been used as a cell immobilization material for many years due to the stable hydrogels formed with mild gelling conditions. However, the alginate acts only as a neutral agent suspending cells or cell aggregates in three dimensions. By modifying this polysaccharide structurally in the manners discussed above and optionally with cell attachment peptides, growth factors, hormones or ECM binding sequences, for example, the alginate can be transformed into a dynamic, interactive matrix capable of guiding cellular gene expression in space and time. The ability to control the viscoelastic properties of the alginate is an integral aspect in guiding cellular gene expression (see M. Opas, Substratum Mechanics and Cell Differentiation. International Review of Cytology, Vol. 150, p. 119–137 (1994); and G F Oster, J D Murry, and A K Harris, Mechanical aspects of Mesenchymal Morphogenesis, Journal of Embryology and Experimental Morphology, Vol. 78, p 83–125 (1983)) and can be used in model in vitro cell culture systems and tissue engineering applications.

Matrices play a central role in tissue engineering. Matrices are utilized to deliver cells to desired sites in the body, to define a potential space for the engineered tissue, and to guide the process of tissue development. Direct injection of cell suspension without matrices have been utilized in some cases, but it is difficult to control the placement of transplanted cells. In addition, the majority of mammalian cell types are anchorage dependent and will die if not provided with an adhesion substrate.

Alginate materials in polymerized form and/or crosslinked and/or modified with bioactive molecules, as discussed above, can be advantageously used as matrices to achieve cell delivery with high loading and efficiency to specific sites. The materials according to the invention also provide mechanical support against compressive and tensile forces, thus maintaining the shape and integrity of the scaffold in the aggressive environments of the body. This is particularly the case when the alginate is crosslinked to a higher degree. The scaffold provided by these materials may act as a physical barrier to immune system components of the host, or act as a matrix to conduct tissue regeneration, depending on the design of the scaffold.

The first type of scaffolds, immunoprotective devices, utilize a semipermeable membrane to limit communication between cells in the device and the host. The small pores in these devices, e.g., (d<10 µm) allow low molecular weight proteins and molecules to be transported between the implant and the host tissue, but they prevent large proteins (e.g., immunoglobulins) and host cells (e.g., lymphocytes) of the immune system from entering the device and mediating rejection of the transplanted cells. In contrast, open structures with large pore sized, e.g., (d>10 µm) are typically utilized if the new tissue is expected to integrate with the host tissue. The morphology of the matrix can guide the structure of an engineered tissue, including the size, shape and vascularization of the tissue.

As discussed above, the alginate, alginate analogue and modified alginate materials of the invention are useful for cell transplantation matrices. These materials can be used to provide such a matrix in any of several ways. For instance, when the matrix is desired to be a temporary matrix for replacement by natural tissue, the material can be designed for biodegradability and system release, for example, by providing hydrolyzable linkages, using relatively low molecular weight alginate chains, biodegradable crosslinking agents, biodegradeable polymer backbones and/or low molecular weight polymer backbone sections. Alternatively, when less degradable matrices are desired, non-hydrolyzable linkages, alginate chains of higher molecular weight, non-degradable crosslinking agents and/or higher molecular weight polymer backbone sections can be used. The many ways in which the properties of the materials can be altered provides a high degree of controllability in providing materials which meet the requirements for the specific application.

In a less degradable form, the matrices can be introduced to the body without cells, but cells will migrate into the matrix, in vivo, and regenerate therein. The alginate or analogue material can be provided in an injectable form, optionally bound to appropriate viable cells, after injection in which case endogenous divalent metal cation in the physiological system after injection causes gelation of the alginate portions of the material. Alternatively, divalent metal cations are added to the solution, for example as a calcium sulfate solution, just prior to injection. As discussed above, the material can be designed to control its rate of gelation to match the ultimate utility. Such injectable solutions can be utilized for delivery of cells to regenerate urologic tissues, for reconstructive surgery, skin replacement, other orthopedic applications or other tissue replacement or repair applications. The alginate-containing materials provide a highly structured, gelled or highly viscous matrix in which the cells are compatible and grow to achieve their intended function, such as tissue replacement, eventually replacing the matrix.

As such, the materials, particularly the polymeric type, may act as analogs to natural glycosamine-glycans and proteoglycans of the extracellular matrix in the body. Furthermore, they can be used to provide preformed gelled or highly viscous matrices bound to cells which may then be surgically implanted into a body. It is of particularly surprising advantage that the materials can be used to implant a matrix which does not contain cells and subsequently the cells can be seeded into the matrix in vivo. The materials optionally may be provided, for example, as a gel, as a viscous solution, as a relatively rigid body, as preformed hydrogel, within a semi-permeable membrane, within microcapsules, etc., and the polymer properties controlled as discussed above to facilitate such applications. The utility of the polymers for cell transplantation and tissue engineering is a significant advance in the art, particularly since it was previously considered not to be practical or possible to achieve such results with synthetic materials; see C. Ezzell, *The Journal of NIH Research*, July 1995, Vol. 7, p. 49–53.

The materials are also advantageously useful as vehicles for drug delivery particularly for sustained release. For drug delivery application, it is useful that the bioactive molecule, i.e., the drug, be linked to the alginate polymer and/or analogue material by a degradeable bond chosen for controllable release in the system. Other utilities of the materials which may or may not employ a bound biological molecule include, for example, wound dressings, wound healing matrix materials, matrices for in vitro cell culture studies, replacements for conventional industrial alginates used, for instance, as food thickening agents and as printing additives, for example to thicken inks, and similar uses wherein the above-described properties are desired. One particularly advantageous use of the crosslinked materials, not necessarily containing bioactive components, is as highly absorbent materials. Particularly, materials with a low extent of crosslinking, e.g., about 1–20% crosslinking, have this utility. The absorbency property makes them useful, for example, in disposable diaper applications. The controllability of the properties of the synthetic polysaccharides according to the invention and the consistent reproduceability of such selected synthetic polysaccharides makes them particularly advantageous for many applications.

The entire disclosure of all applications, patents and publications, cited above and below, is hereby incorporated by reference.

EXAMPLES

All temperatures are set forth uncorrected in degrees Celsius; and, unless otherwise indicated, all parts and percentages are by weight.

Example 1

The following scheme demonstrates one method of preparation of an embodiment of the inventive alginates modified with the cell adhesion molecule RGD:

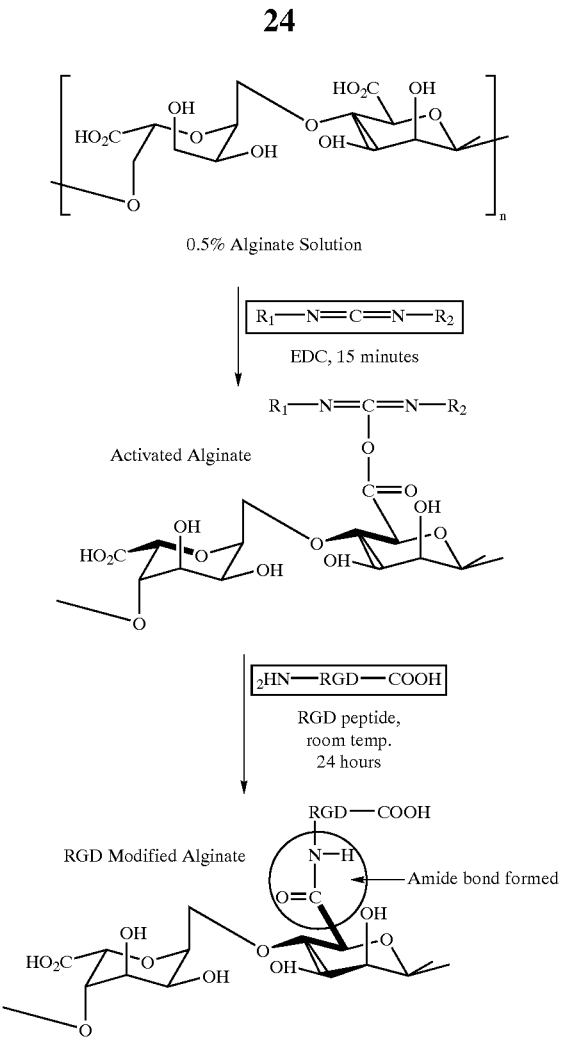

In this reaction scheme for alginate/peptide conjugation, carbodiimide enzyme (EDC) is added to 0.5% alginate solutions. Fifteen (15) minutes are allowed for activation of the carboxylic acid groups on the alginate backbone. The RGD containing peptide is added to the reaction and allowed to react for 24 hours at room temperature. The reaction is quenched by the addition of 1N HCL which deactivates the EDC. The solution is brought back to pH 7 with addition of 1M NaOH and extensively dialyzed over 3 to 5 days, removing unreacted chemicals. The polymer is then redissolved in water and sterile filtered.

Example 2

A pentapeptide (GRGDY) was used as the model cell adhesion peptide. The N-terminal free amine provides a site for coupling to alginate, while the C-terminal tyrosine provides a site for iodination (forming $^{125}$I-labeled peptide), which allows the coupling reaction to be quantitatively analyzed.

Figure 1:
FIG. 1 provides examples of useful configurations of the polymeric backbone sections with side chains.
Figure 1:
Figure 1:
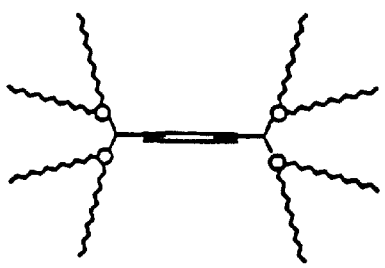
Figure 1:
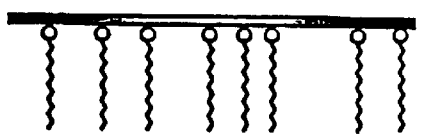
Figure 1:
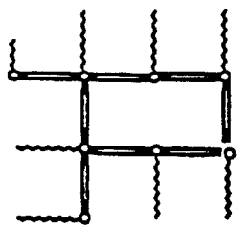
Figure 1:
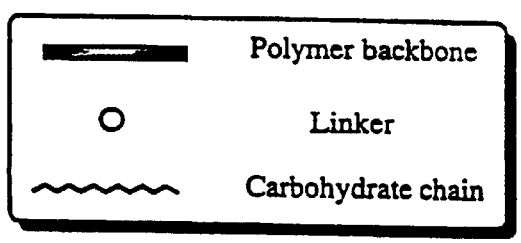
Figure 2:
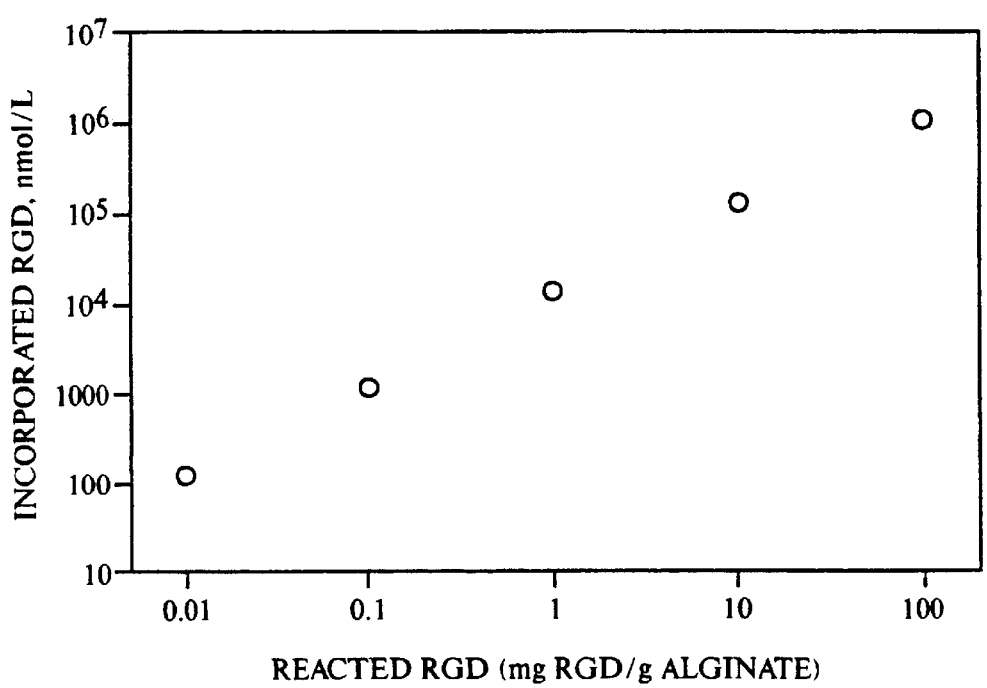
FIG. 2 provides an example that the density of cell adhesion ligands can be readily varied over a 5-order of magnitude density range.

All peptides were synthesized at the University of Michigan Peptide Core Facility, and the starting alginate (unmodified) was purchased from ProNova. Covalent peptide grafting onto the alginate polymer backbone is done in a 1% (w/v) alginate solution in a 0.1 M 2-(N-morpholino)-ethanesulfonic acid (MES) buffer containing 0.5 M NaCl. N-hydroxysulfosuccinimide (Sulfo-NHS) is used as a co-reactant greatly increasing EDC efficiencies in a similar manner to HOBt. Sulfo-NHS is added to the reaction solution followed by the peptide and the EDC. The ratio of uronic acid:EDC:sulfo-NHS is constant, while only the peptide available for reaction is varied. This chemistry consistently gives 65–75% coupling efficiency compared to available peptide as shown in FIG. 2. The solution is allowed to react for 14–18 hours at which time hydroxyl amine is added to quench any unreacted activated sulfo-NHS-esters and reestablishing carboxylates. The solution is extensively dialyzed against water in 3500 MWCO dialysis tubing. Preliminary experiments utilizing $^{125}$I-labeled GRGDY indicate <0.5% of unreacted peptide remains after dialysis, suggesting a relatively pure alginate-peptide product. The dialyzed solution is sterile filtered, lyophilized and stored dry until use. A recently described technique (Klock et al., *Appl. Microbiol. Biotechnol.* 40:638–643, 1994) can be used to detect any polyphenol contaminants in the alginate.

Surface modification only of alginate hydrogels will be done for two-dimensional cell culture experiments to save on reagents. This process is done under sterile conditions with all reactants in sterile filtered aqueous solutions. The reaction may be done in the above MES buffer or in diH$_2$O with subsequent 10-fold loss of reaction efficiency. $^{125}$I experiments show similar reaction efficiencies to the bulk modified alginate. Cross-linked alginate gels are cast between parallel glass plates with 2mm spacers and disks are punched out with circular punches. Ten to twelve disks are added to 50 ml centrifuge tubes with 40 mls reaction solution with the reactants at the same ratios as above. The disks are extensively washed in water, and then DMEM before being placed in 24-well plates for cell experiments.

The reaction conditions have been optirized by variation of the reaction buffer, pH, EDC:uronic acid ratio, and efficiencies of peptide incorporation between 65 and 75% are typically obtained. The density of cell adhesion ligands, a critical regulator of cellular phenotype following adhesion to a biomaterial can be readily varied over a 5-order of magnitude density range. Both surface coupling, as well as bulk coupling of alginate can be readily obtained with this approach.

Example 3

Figure 3:
FIG. 3 provides an example of the adhesion of 3T3 fibroblasts and skeletal myoblasts to alginate matrices in culture.

The adhesion of 3T3 fibroblasts and skeletal myoblasts to alginate matrices has been confirmed in culture. See FIG. 3, while no cell adhesion is noted on control alginate surfaces without adhesion ligands, even in serum containing medium. Furthermore, skeletal myoblasts exhibit a differentiated phenotype on these matrices. Since unmodified alginate hydrogel surfaces do not support cell adhesion, this data suggests that insoluble ECM signaling for cell differentiation can be partially provided through coupling of cell adhesion ligands.

Example 4

The following scheme demonstrates one method of preparation of the inventive polymeric backbone materials:

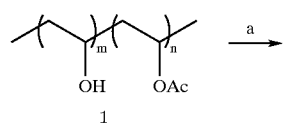

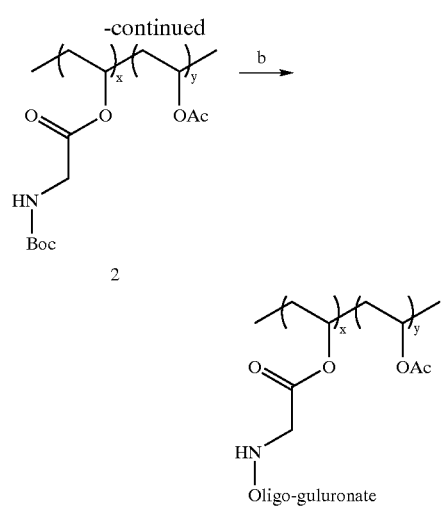

This scheme displays an example of the synthetic pathways that can be used for the synthesis of the graft copolymers. Oligo-guluronate was prepared by partial hydrolysis of alginate with 70% guluronate content. Hydrolysis occurred preferentially at the alternating region (M/G region), therefore, a mixture of oligo-mannuronate and oligo-guluronate resulted. The latter was separated from the other oligomer by differential solubility at highly acidic conditions. See Penman A, Sanderson G R (1972): A method for the determination of uronic acid sequence in alginates. *Carbohydr Res* 25:273:282 and Haug A, Larson B, Smisrod O (1966): A study of the constitution of alginic acid by partial acid hydrolysis. *Acta Chem Scand* 20:183–190. PVA, (poly(vinyl alcohol)) was coupled to Boc-glycine in the presence of dicyclohexyl carbodiimide. The amount of Boc-glycine in the reaction mixture controls the branching ratio of the resulting graft copolymers in later steps. The Boc protecting group was removed under acidic conditions and subsequent grafting of oligo-guluronate by reductive amination of the reducing end of carbohydrate with the amino group of glycine on PVA furnished the desired copolymers.

Example 5

Backbone: Poly(allylamine) PAM Hydrochloride

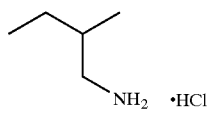

Molecular formula of repeating unit: C3H8NCl

Molecular weight of repeating unit: 93.5

Molecular weight (Mn) reported by Aldrich: 50,000–65,000 i.e., # of repeating unit on each polymer molecule: 535–695

Nondegradable from of backbone.

Side Chain: Oligo-guluronate(Gul)

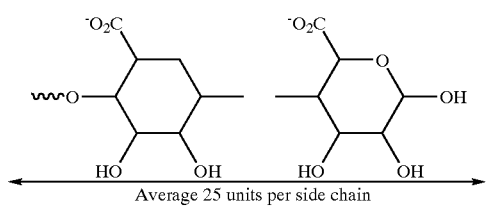

Average 25 units per side chain

Each of the sodium guluronate units has 198 MW. so 25 units has MW of 4950, i.e., ~5000

Comb Polymers PAM-Gul by Direct Linking of Backbone to Side Chains

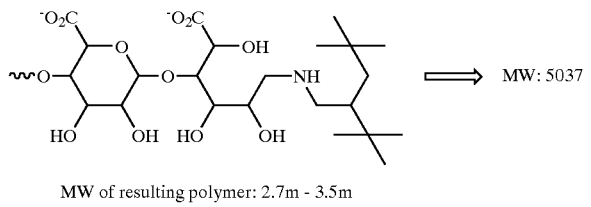

MW of resulting polymer: 2.7m - 3.5m

Incorporation of the side chains was controlled by the ratio of Gul to PAM so as to provide polymers with 100%, 50% and 10% of sites on backbone having side chain.

Example 6

Acrylic Polymer Backbone

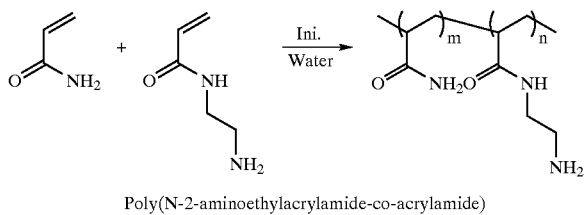

Poly(N-2-aminoethylacrylamide-co-acrylamide)

Carbohydrate Incorporation

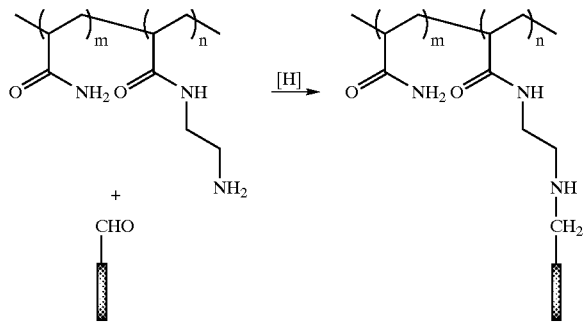

Other Backbones

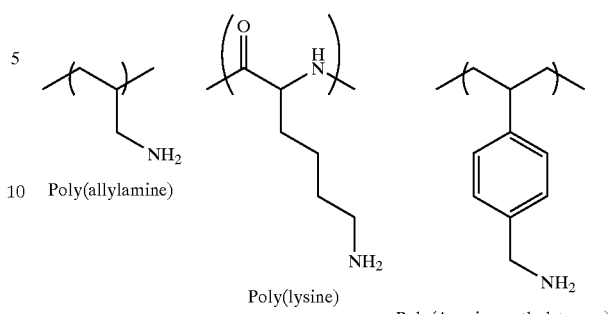

Poly(allylamine)

Poly(lysine)

Poly(4-aminomethylstyrene)

Example 7

Polyethylene glycol (PEO) backbone (see scheme of Example 8) with branched linker group to provide dendritic polymers when polysaccharide side chains are added. The dendritic polymers may form networks by coordination of calcium ions between side chains of two or more differing dendritic polymers. The linker group is hydrolyzable, and thus degradable.

Example 8

Dendritic polylysines as the polymeric backbone for incorporation of G-block alginate chains where prepared as shown in the following schematic. The amino groups of lysine was protected by Boc group while the carboxyl end was unprotected for peptide coupling which was achieved by DCC/HOBt chemistry. PEO (8000 Mw) was first coupled to hydroxysuccinamide ester of di-Boc protected lysine in dichloromethane. The ether-washed polymer was dissolved into 25% TFA in $CH_2Cl_2$ to remove Boc group. Precipitation into ether furnished the deprotected peptide ready for next cycle of coupling. Coupling of the corresponding free polyamines on the polymer support with excess DCC/HOBt-activated di-Boc-lysine furnished PEO-linked G-1, G-2 and G-3 dendrimers, respectively, after crystallization from ether. Cleavage of the peptides from the polymer supports was achieved by treating the PEO-peptide conjugate in methanol with hydrazine for 1 hour producing the hydrazone peptide dendrimers in good yields. In addition, G-2 dendrimer with a free hydroxyl end was also prepared by treating with aqueous sodium hydroxide solution in methanol for 1 hour. PEO-Gn (n=0–3) gave satisfactory proton and carbon NMR spectra. Purity and structures of G-2 and G-3 dendrimers were established by TLC, elemental analysis and $^{13}$C-NMR spectroscopy.

In summary, a G-3 dendritic polylysine (15 L-lysine units) of molecular weight 3096 was synthesized rapidly in 7 steps. We have designed these dendrimers to couple G-block chains via their hemiacetal terminus. This was accomplished by reductive amination using sodium cyanoborohydride.

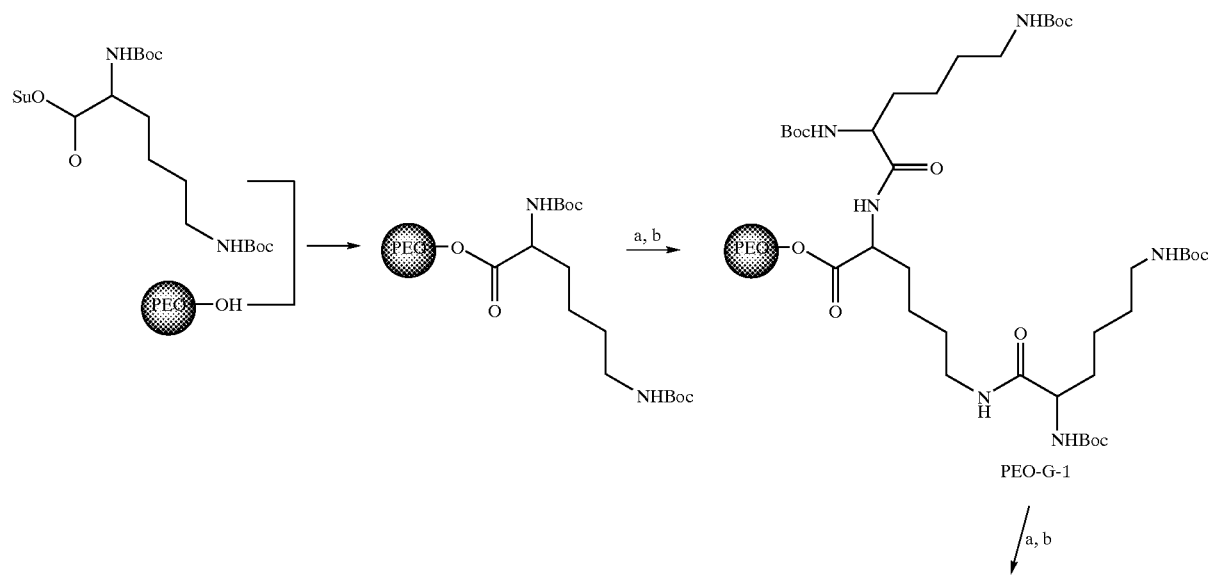
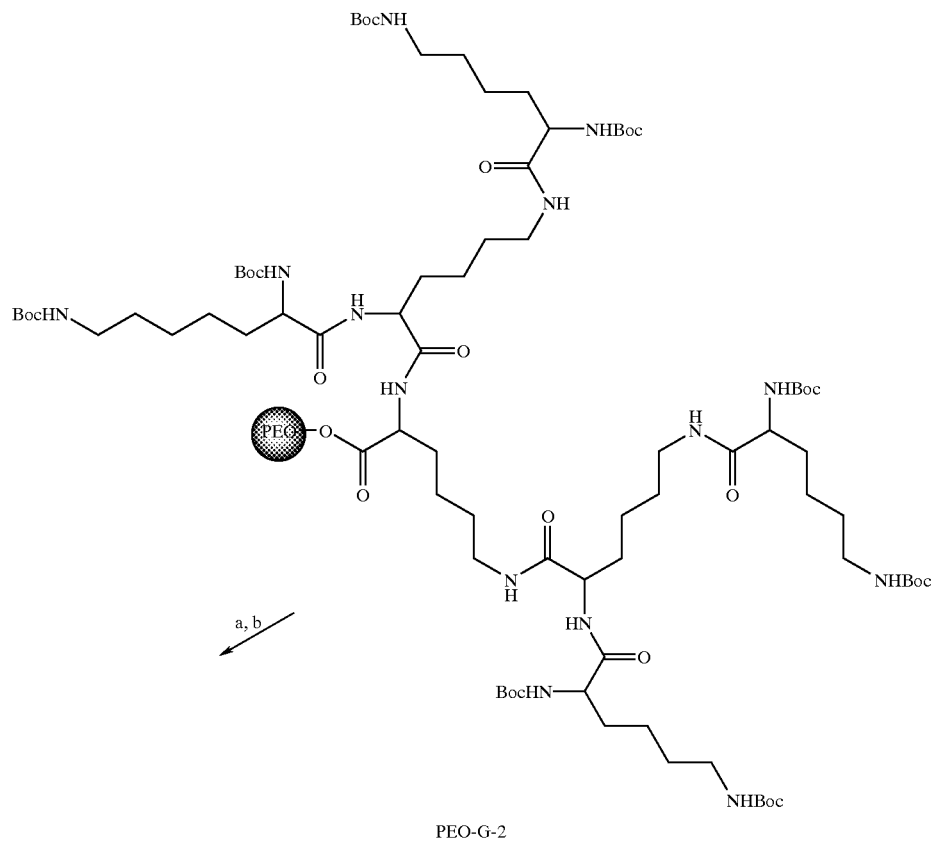

-continued

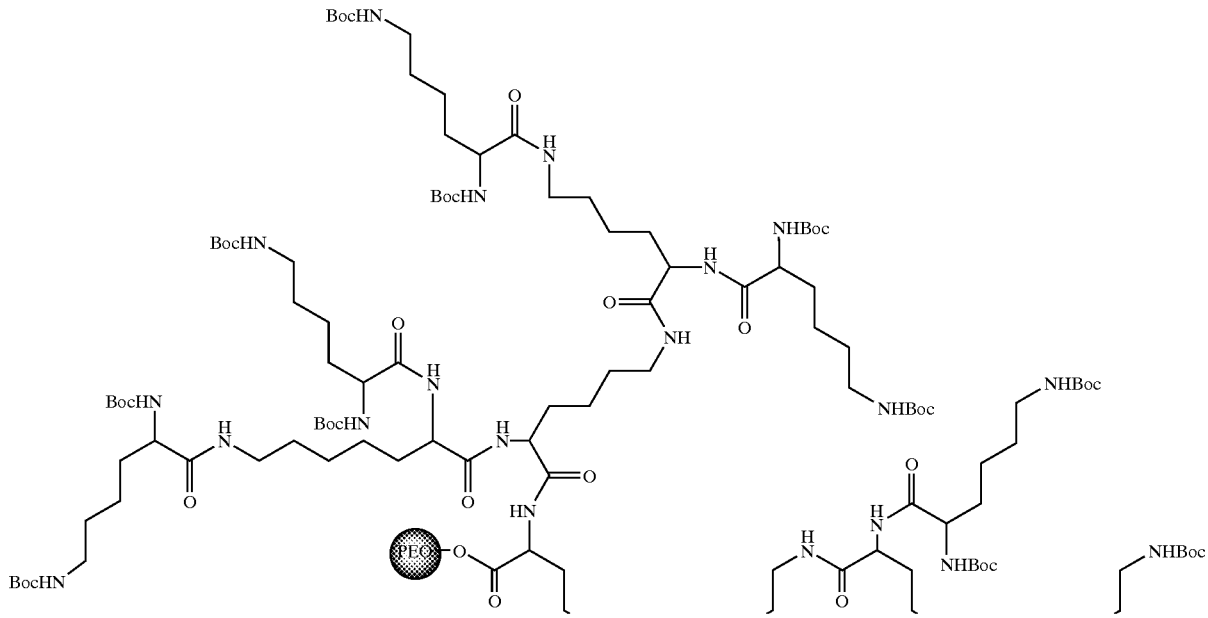

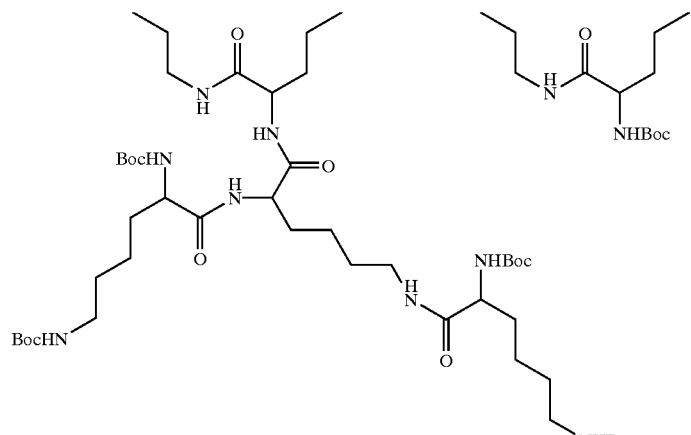

PEO-G-3

Synthesis of PEO-Lysine dendrimer. a) TFA, CH$_2$Cl$_2$ b) L-lysine, DCC, HOBT, CH$_2$Cl$_2$.

Example 9

Comb polymers were prepared using poly(vinyl alcohol) (P)VA). PVA belongs to a class of water-soluble polymers whose properties can be varied widely. PVA cannot be synthesized directly due to the instability of its monomer. Deacetylation of poly(vinyl acetate) through alcoholysis, hydrolysis or aminolysis leads to PVA's. The hydrophilicity and water solubility can be readily controlled by the extent of hydrolysis and molecular weight of the poly(vinyl acetate) used. PVA is not truly biodegradable, due to a lack of labile bonds, but PVA with a molecular weight <20K can be cleared through the kidneys and has been used as drug delivery matrices and surgical prosthesis.

PVA (MW=9000–10000, 80% hydrolyzed) can be esterified in DMF with Boc-Glycine using the DCC coupling method, shown in the following schematic. By varying the ratio of hydroxyl groups in the PVA to the amount of carboxylic groups in the Boc-glycine different degrees of grafting (i.e. 0.8, 0.25 and 0.16) can be obtained. The amino-protecting group (Boc) can be removed by utilization of trifluoroacetic acid in CH$_2$Cl$_2$. The polymer is characterized by standard laboratory methods such as TLC, FT-IR, $^1$H-NMR and aqueous SEC. In a second reaction step the amino functionalized PVA can be covalently coupled through reductive amination to oligoguluronate.

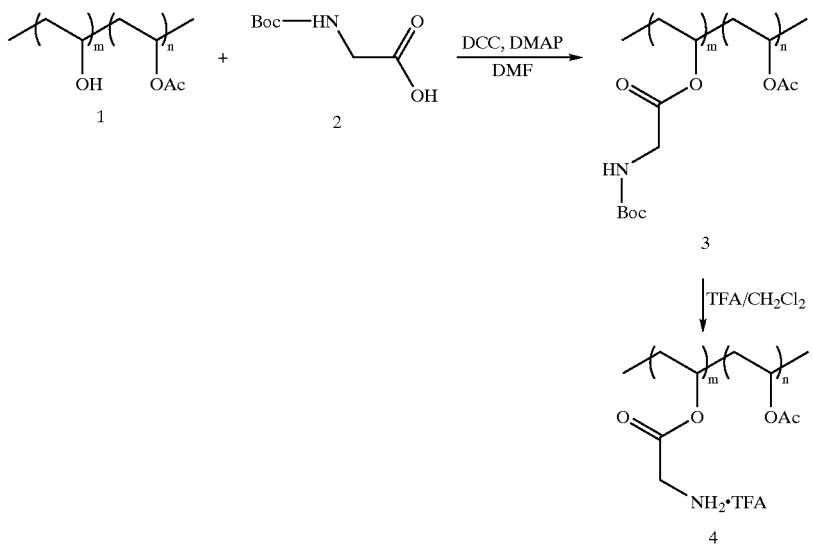

Esterification of PVA 1 with Boc-Glycine 2 in DMF and subsequent deprotection with trifluoroacetic acid in $CH_2Cl_2$.

Example 10

Preparation 1—Five stock solutions of aqueous sodium alginates (2%) were prepared in Erlenmeyer flasks. Lysine ethyl ester was added to each solution to yield the following ratios: 0, 25, 50, 100, 150% lysine:uronic acid mole ratio. EDC and HOBT in twice the amount of moles of lysine each were added to each solution. The mixtures were thoroughly mixed and poured over petri dishes. Calcium sulfate powder was then added to gel the solutions for 24–48 hours. Circular discs were made from each batch, washed with distilled water, and lyophilized. The dimensions and weights of each disc was measured before and after lyophilization.

Preparation 2—Several stock solutions of aqueous sodium alginates (2%) were prepared in Erlenmeyer flasks. The selected amount of lysine ethyl ester (0, 25, 50, 100, 150% lysineuronic acid mole ratio) was added to each solution and stirred for 24 hours. Each solution was poured into a petri dish to form a layer 3 mm in diameter. Calcium sulfate powder was then added to the surface of the layers to induce gelling. After the gels hardened (24–48 hr.), circular disks were cut from all the gels. Each set of discs were transferred into a test tube. EDC and HOBT were then added (lysine:EDC:HOBT 1:2:2 mole ratio) to each tube. The disks were shaken for 24 hours and rinsed with distilled water. The dimensions and wet-weight of each disk were recorded. Each disc was then frozen, and lyophilized, and the dimensions and dry-weight of each disk were recorded afterwards.

Study 1: Alginate gels prepared using various combinations of reagents (see Table A) using preparation 2, are tested for their ability to maintain their structure following chelation of calcium by exposing to a solution of sodium citrate. Control alginate gels (non-crosslinked) dissolved as expected. Protected t-boc lysine was utilized as a control in this study as the amino groups in the lysine are protected and cannot couple to the carboxylic acid groups of the alginate. Alginate gels cross-linked with lysine using EDC alone did not dissolve, but did expand in size following calcium chelation. Alginate gels cross-linked using EDC and HOBT maintained their original dimensions. These results confirm that cross-linking of alginate gels leads to matrices in which the structure can be maintained independently of divalent cation cross-linking, and also suggest that the presence of HOBT stabilizer improves the cross-linking.

TABLE A

| Gel Components | Result following calcium chelation |
| --- | --- |
| Alginate + lysine | dissolved |
| Alginate + lysine + EDC | swelled in size, but did not dissolve |
| Alginate + lysine + EDC + HOBT | maintained size and shape |
| Alginate | dissolved |
| Alginate + t-boc lysine + EDC | dissolves |

Study 2: Alginate gels were cross-linked by method 2 using various ratios of alginate to lysine in order to determine if there was a dose dependency of gel stability on lysine content. Gels cross-linked with EDC alone (no HOBT) and EDC+HOBT were exposed to sodium citrate and examined for swelling or dissolution. Gel dissolution and stability was a function of lysine content and cross-linking conditions as shown in Table B.

TABLE B

| Lysine content (% alginate functional groups) | Cross-linked with EDC alone | Cross-linked with EDC + HOBT |
| --- | --- | --- |
| 0 | dissolved | dissolved |
| 25 | dissolved | dissolved |
| 50 | did not dissolve, but swelled to dimensions of container | mild swelling |
| 75 | mild sweillng | maintained size and shape |
| 100 | mild swelling | maintained size and shape |
| 150 | small amount of swelling | maintained size and shape |

Figure 4:
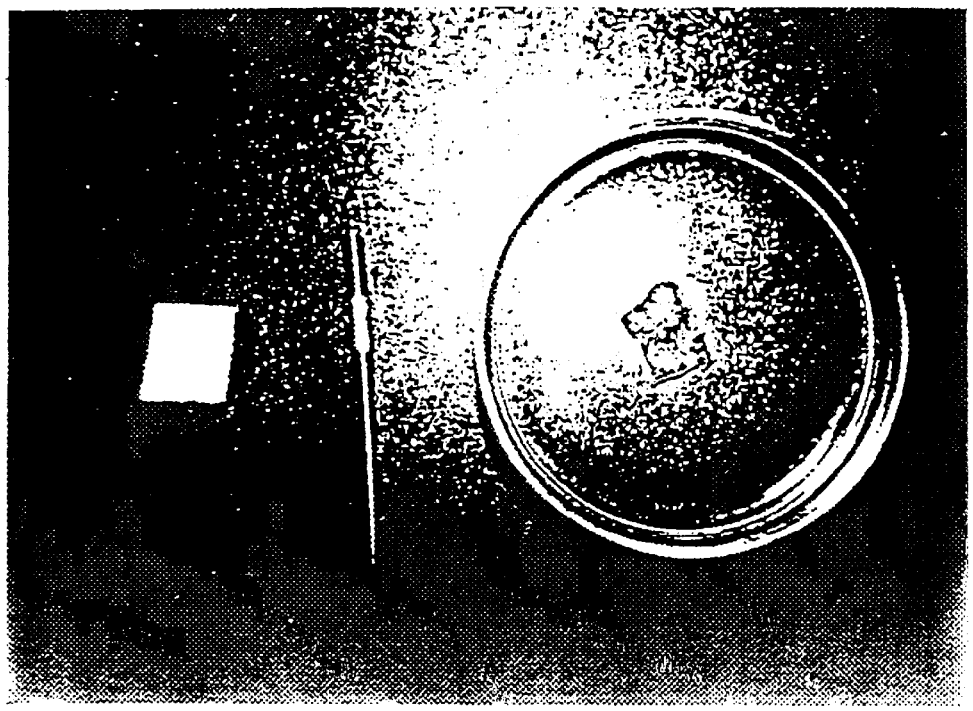
FIG. 4 shows alginate gels cross-linked with lysine and cut into slabs for testing their shape memory.

Study 3: Alginate gels cross-linked with lysine (100% lysine content, cross-linking with EDC and HOBT) were cut into slabs (initial volume 576 $mm^3$), lyophilized and then tested for their shape memory (see FIG. 4). The dried matrices (right side of figure) were compressed and placed in tubing (middle of the figure) with an inner diameter of 1.56 mm (approximately 4.5 French—a tubing diameter typically utilized for endoscopic procedures), and pushed through a 5 cm long portion of the tubing. The matrices were then placed in a petri dish containing water and observed over time. These matrices returned to a slab geometry (left side of the figure) after 1 hour, and obtained a volume of approximately 400 mm$^3$ (approximately 70% initial volume) by this time. The ability of these matrices to return to their approximate size ad shape after this severe compression indicates they have significant shape memory.

Figure 5:
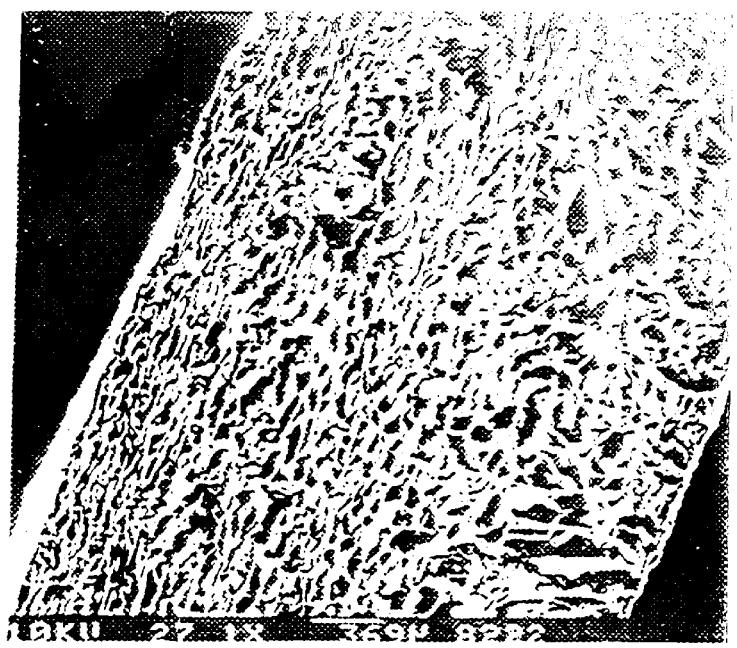
FIG. 5 shows scanning electron microscopy examination of crosslinked alginate matrices revealing a highly porous material with large pores.

Study 4: An important feature of the cross-linked matrices is their ability to be seeded with cells after preparation. Cross-linked alginate gels (100% lysine content, EDC+HOBT to cross-link) were lyophilized and sterilized. Scanning electron microscopy examination of matrices revealed a highly porous material with large pores (FIG. 5). The matrices were placed in a suspension of smooth muscle cells in tissue culture medium (DMEM supplemented with 10% calf serum), and examined for cell infiltration. Observation of matrices with a microscope indicated that the cell suspension absorbed into the cross-linked alginate matrices, and this resulted in a distribution of cells throughout the matrices (not shown in figure).

Study 5: 2% alginate gels were crosslinked with lysine (100% lysine) using method one, however, 10-fold EDC and 5-fold HOBT concentrations were used to optimize crosslinking. 20 g (approximately 20 mls) of 2% alginate solution were added to 50 ml conicals and selected lysine (0%, 1%, 10%, 25%, 50% and 100% lysine compared to alginate monomer units) and HOBT amounts were added. The solutions were mixed well, then appropriate amounts of EDC were added. Immediately following the addition of EDC, 0.168 grams calcium sulfate was added and the conicals were shaken vigorously for 10 to 20 seconds prior to pouring the solution. The gels were cured for 3 hours between parallel plates about 2.5 mm apart. Disks were then punched out and added to either sodium citrate (to remove the calcium) or 0.1 M calcium chloride for 10 minutes prior to storage in distilled water. Gel stability with removal of calcium and mechanical testing were done with all conditions.

| % Lysine | removal of calcium with sodium citrate | compressional modulus (gels with calcium) | compressional modulus (calcium removed) |
|---|---|---|---|
| 0% | dissolved | 6.4 N/mm | dissolved |
| 1% | dissolved | 4.6 N/mm | dissolved |
| 10% | dissolved | 3.58 N/mm | dissolved |
| 25% | mild swelling | 1.04 N/mm | 0.143 N/mm |
| 50% | little swelling | 0.55 N/mm | 0.174 N/mm |
| 100% | little swelling | 0.32 N/mm | 2.02 N/mm |

The dose dependency of the lysine content from study 2 was reconfirmed, but the extent of crosslinking was increased as suggested by complete stability of the 25% and greater crosslinked gels upon calcium removal The compressional modulus of the gel disks decreased with increasing lysine content likely due to the lysine disruption of the calcium binding sites in the alginate. Interestingly, upon calcium removal with sodium citrate, the modulus of the gel disks increase with increasing lysine content.

Example 11

Alginate cross-linking with diamines is performed in a 0.1 M MES buffer of pH 7 with 0.3 M NaCl. The chemistry has been optimized for maximum cross-linking with the variables pH, [NaCl], and EDC:HOBt:uronic acid ratio. EDC reacts with the carboxyl group of the uronic acid creating an activated ester intermediate which is reactive towards amines. A major competing reaction with amide bond formation is hydrolysis of the EDC intermediate by water, and the EDC intermediate half-life is on the order of seconds (Hermanson, 1996, cited above). However, the addition of coreactants like HOBt or N-hydroxysulfosuccinimide will react with the EDC activated ester creating longer lasting intermediates leading to greater reaction efficiencies (Hermanson, 1996, cited above).

Example 12

The reaction scheme for PEG cross-linking molecules, shown below involves adding equimolar amounts based on alcohol groups of poly(ethylene glycol) (1) and N-protected amino acid (2), and esterifying via direct coupling by DCC and DMAP in $CH_2Cl_2$. Deprotection of the BOC protecting group in compound (3) is performed by utilization of trifluoroacetic acid (TFA). Cross-linking reactions between the carboxylic group of the alginate and the primary amino groups of the modified PEG molecule are carried out by the formation of an hydroxy benzotriazole active ester in situ and the consequent addition of the coupling agent EDC. The functionalized PEG's were purified by liquid column chromatography and characterized utilizing standard laboratory methods such as TLC, FT-IR, $^1$H-NMR and elemental analysis. The molecular weight distribution as well as structural information of the polymers will be determined by GPC measurements in aqueous solution. We are utilizing a relatively new analytical technology known as $SEC^3$ (RI, Viscometer, RALLS) to obtain absolute molecular weights thus eliminating the assumption that standard and sample have the same molecular structure.

Poly(ethylene glycol) with molecular weights MW 200, 400, 600, and 1000 was obtained from Lancaster Synthesis Inc., PEG with MW 3400 and 1,3-Dicyclohexylcarbodiimide (DCC) were from Aldrich chemical company. N-t-boc-glycine (98%), trifluoroacetic acid and 1-ethyl-3-[3-dimethylamino-propyl]carbodiimide (EDC) were ordered from Sigma, St. Louis, Mo.

(A)

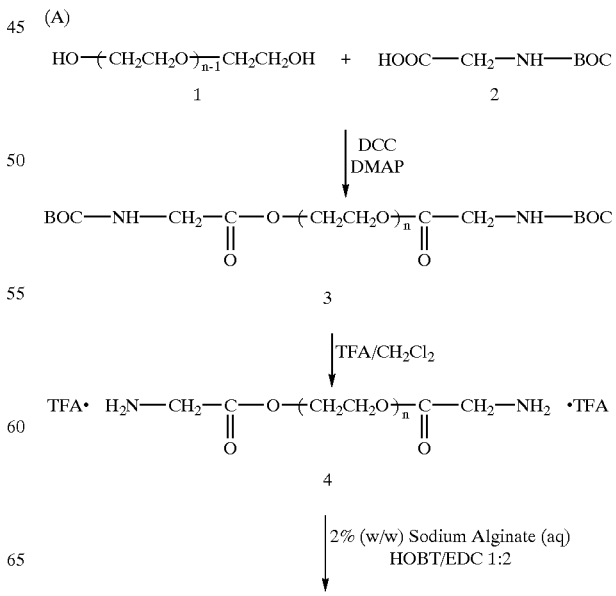

(B)

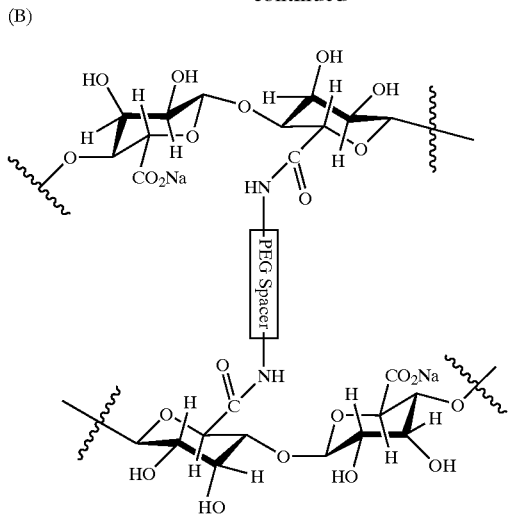

(A) Synthesis of amino terminated Poly(ethylene glycol)s with various repeat units n ranging from 4.5–77.3 (MW=200, 400, 600, 1000, 3400).

(B) Reaction of PEG-cross-linker molecule with sodium alginate.

The reaction solutions are cast between parallel glass plates for 12–16 hours and defined shapes may be cut from these hydrogel sheets. Defined shapes may also be formed by casting the reacting solution into a mold of the desired shape, and allowing the cross-linking reaction to occur. The resultant hydrogels are characterized for mechanical properties (elastic modulus, shear modulus, maximum true stress, maximum extension), and swelling properties. The methyl ester of lysine and modified amino terminated PEG of molecular weights 200, 400, 600, 1000 and 3400 was used to cross-link alginate in ratios of amino:carboxylic groups 3–50%.

Example 13

Figure 6:
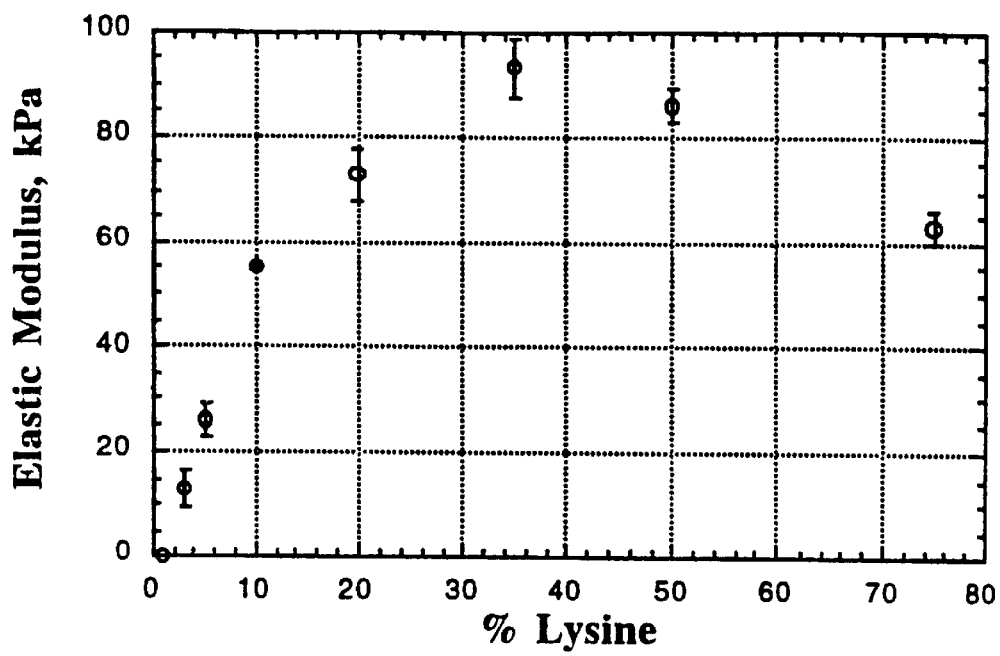
FIG. 6 is a graph showing that the mechanics of the hydrogel network can be controlled by varying the amount of lysine available for cross-linking.

Lysine cross-linked alginates. The alginate hydrogels were cross-linked with the methyl ester of lysine. The carbodiimide chemistry was optimized for maximum effective cross-linking at any given lysine content by varying pH, ionic strength of the reaction buffer, and the EDC:HOBt:uronic acid ratio. The mechanics of the hydrogel network can be controlled by varying the amount of lysine available for cross-linking (FIG. 6). The elastic modulus of the hydrogels increases with increasing lysine content up to 35%, but then decrease with additional lysine added. This decrease in modulus is attributed to an increase in network defects including more dangling half-reacted lysines and elastically ineffective loops which do not contribute to the mechanical properties of the network, and in this case actually detract from the mechanics due to the shear number of defects.

The mechanical properties, including stiffness shown by the elastic modulus, as well as strength and elasticity, can be controlled by varying the amount of lysine available for reaction.

Figure 7:
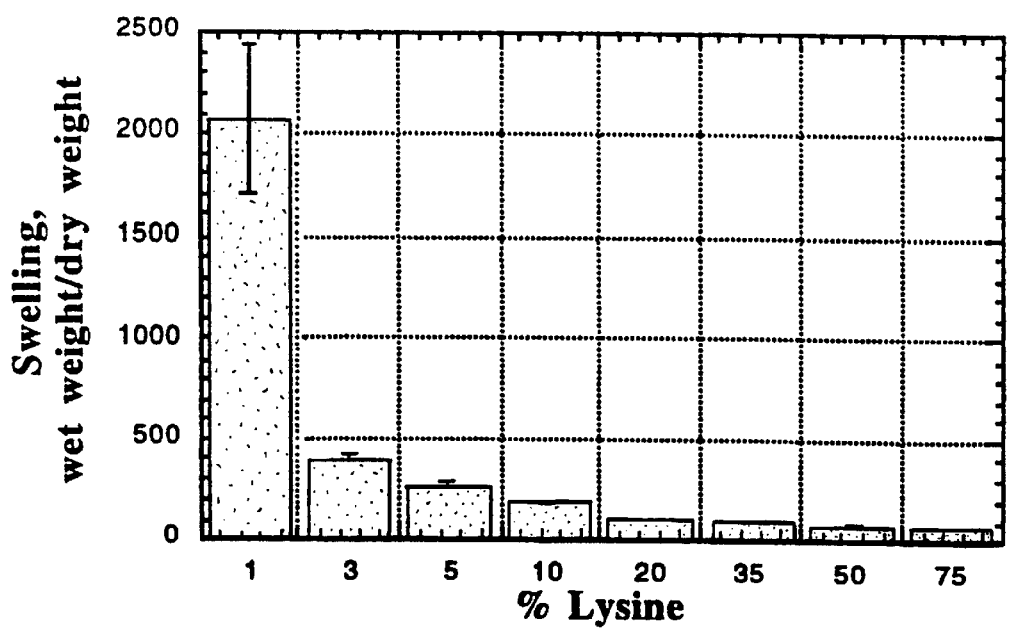
FIG. 7 is a graph showing that the swelling ability of lysine crosslinked alginate hydrogels decreases with increased crosslinking.

The swelling capabilities of the lysine crosslinked hydrogels were determined by measuring the volume of water a known mass of crosslinked alginate absorbs. Swollen hydrogel disks were cut to 15.7 mm in diameter, dried with a towel, and weighed to determine the weight of the water and polymer. The disks were then frozen and lyophilized to remove all of the water from the hydrogels, leaving highly porous fluffy disks after lyophilization. The initial wet weight of the hydrogels was divided by the dry weight of the dried disks to determine the swelling ratio (FIG. 7). Swelling ability of lysine crosslinked alginate hydrogels decreases with increased crosslinking. Lightly cross-linked alginates absorb over 2000× their mass in water, suggesting they will be useful as superabsorbent materials (e.g., in disposable diapers). The more highly crosslinked gels absorbed approximately 70 times their weight in water, with intermediate crosslink densities ranging between these two extremes. The dry disks were then rewet with diH$_2$O over 48 hours and weighed to determine if the lyophilized disks were able to absorb comparable amounts of water that they initially held. The lyophilized disks were able to absorb similar amounts of water that they initially held +/− about 10%. The more highly crosslinked gels (75% lysine) absorbed approximately 10% less water and the lightly crosslinked gels (1–20% lysine) absorbed 10% more than initially measured. On drying, the alginate network phase separates to make a highly porous sponge. The hydrated network microstructure does not seem to reform immediately upon rehydration, as much of the water soaked up by the sponges may be removed by placing the sponge on a towel within the first few hours after rehydration. However, after 48 hours of soaking very little water may be removed from the from the structure when exposed to a drying towel suggesting the hydrated network structure returns.

Example 14

Highly cross-linked alginate matrices exhibit shape memory properties advantageous for certain applications. Lyophilized alginate matrices act as hydrophilic sponges when exposed to water, hydrating almost instantly. To demonstrate shape memory properties, 50% lysine crosslinked sponges were compressed, rolled up into tight cylinders and delivered through 3mm ID silicone tubing to mimic endoscopic delivery on the laboratory bench. The rolled up matrices were pushed through the tubing with flexible teflon string (1.3 mm OD), and they returned to their initial shape and dimensions within seconds upon rehydration. The water absorption properties of the compressed disks are similar to noncompressed disks (in the above swelling study) and absorb around 90% of the initial water content after 24 hours.

Example 15

The molecular weight between cross-links in the alginate network was calculated directly from the shear modulus and swelling measurements (Peppas and Merrill, *J. Appl. Polym. Sci.* 21: 1763–1770, 1977) to assess the density of functional cross-links (interchain). This number can then be compared to the total number of cross-links (intra- and interchain) determined chemically. Calculation of $M_c$ was performed utilizing the relationship:

$$G = RTC_r/M_c(1 - 2M_c/M_n)Q^{-1/3} \qquad \text{Equation 1}$$

where G is the shear modulus, R and T are the gas constant and temperature in Kelvin respectfully, $C_r$ is the concentration of the polymer in the cross-linking solution, $M_c$ is the molecular weight between cross-links, and $M_n$ is the number average molecular weight of the native polymer. Q is the swelling ratio defined as $$Q = v_r/v_s \qquad \text{Equation 2}$$

with $v_r$ being the volume fraction of the polymer in the unswollen cross-linked gel and $v_s$ is the volume fraction in the swollen gel. G is obtained from manipulation of the stress-strain data from compression testing by plotting stress versus $-(\lambda - 1/\lambda^2)$ with $$\lambda = L/L_0 \qquad \text{Equation 3}$$

$L_0$ and L being the thickness of the gel before and during compression respectfully.

These calculations indicate that Mc ranges from 1500 for the most highly lysine cross-linked alginates, to approximately 25,000 for the least cross-linked (1% lysine) alginates.

Example 16

Figure 8:
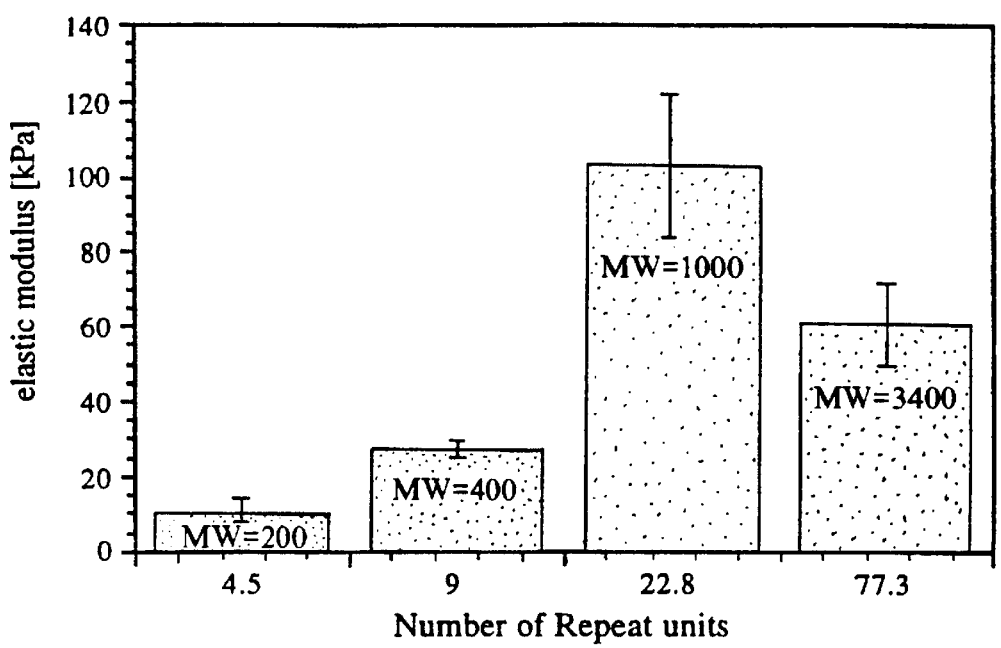
FIG. 8 is a graph showing the elastic modulus in compression [KPa] versus number of repeat units in cross-linking molecule.
Figure 9:
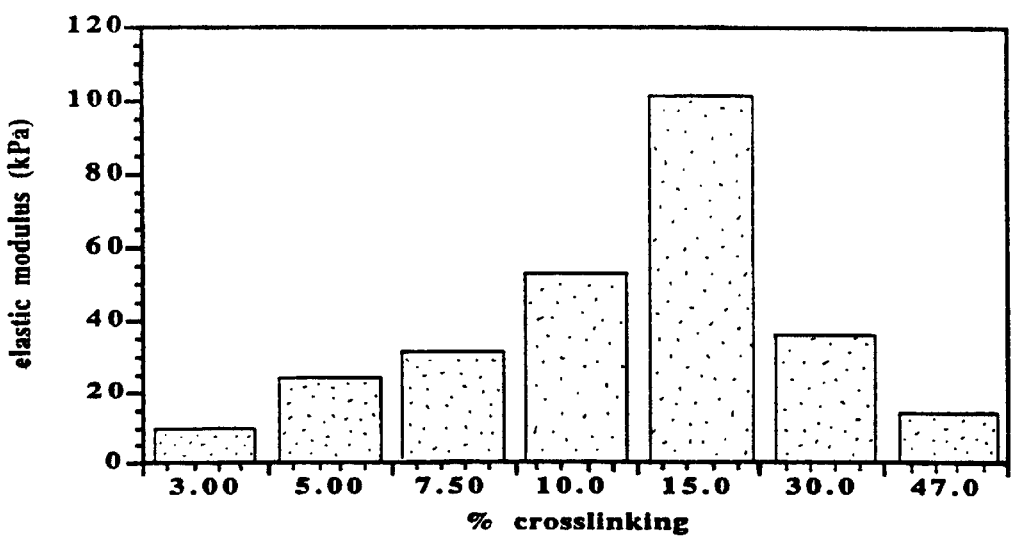
FIG. 9 is a graph showing elastic modulus vs. cross-link density [%] utilizing the PEG of 1000 molecular weight as the cross-linking molecule.

Studies have also been performed to vary the Mc by altering the molecular weight of the cross-linking molecule in polyethylene glycol cross-linked alginates. These studies have utilized PEG diamines synthesized in our laboratories as the cross-linking molecule. The compressive modulus of alginate gels increased with the number of repeat units in the cross-linking molecule up to a molecular weight of 1000. See FIG. 8. Showing the elastic modulus in compression [KPa] versus number of repeat units in cross-linking molecule. An equal molar amount of each monomer was used in each reaction. This may be related to directly to the molecular weight of the cross-linking PEG, or to an increased flexibility of the cross-linking monomer which results in a greater extent of reaction (Allen et al, *Macromolecules*, 22:809–816, 1989). A decrease in the modulus was found with further increase in the cross-linking molecule molecular weight. Varying the cross-link density (utilizing the PEG with 1000 molecular weight), again had a strong effect on the stiffness of the gels. Similar to the results with lysine, an increase in modulus was noted up to a certain cross-linking, but then decreased with additional cross-linking. FIG. 9 showing elastic modulus vs cross-link density [%] utilizing the PEG of 1000 molecular weight as the cross-linking molecule. This decrease in modulus is again likely attributable to an increase in network defects at higher PEG diamine concentrations, including more dangling half-reacted PEGs which detract from the mechanics.

Example 17

Cross-linked polyaldehyde alginates (PAA). An additional approach to covalently cross-link alginates is to oxidize alginate and cross-link it with a bifunctional cross-linker to form hydrogels. Thus, alginate, 1, was derivatized by sodium periodate oxidation, as shown below, at ambient temperatures to yield the limit-oxidized product, 2. The reaction was monitored by the appearance of the aldehydic symmetric vibrational band (carbonyl) via FTIR. Limit-oxidized alginate was then cross-linked via the aldehyde groups with adipic dihydrazide to form hydrogels, 3. This process was followed by the disappearance of the symmetric vibrational band at 1735 cm$^{-1}$.

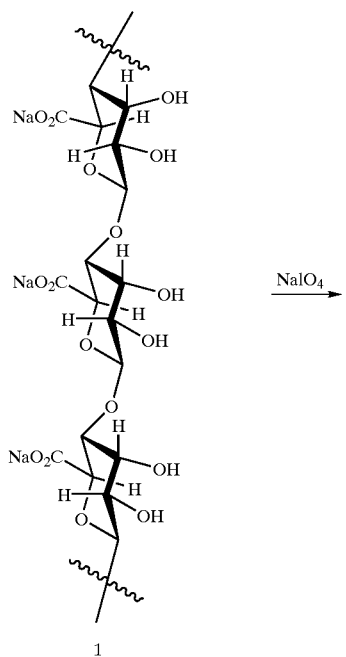

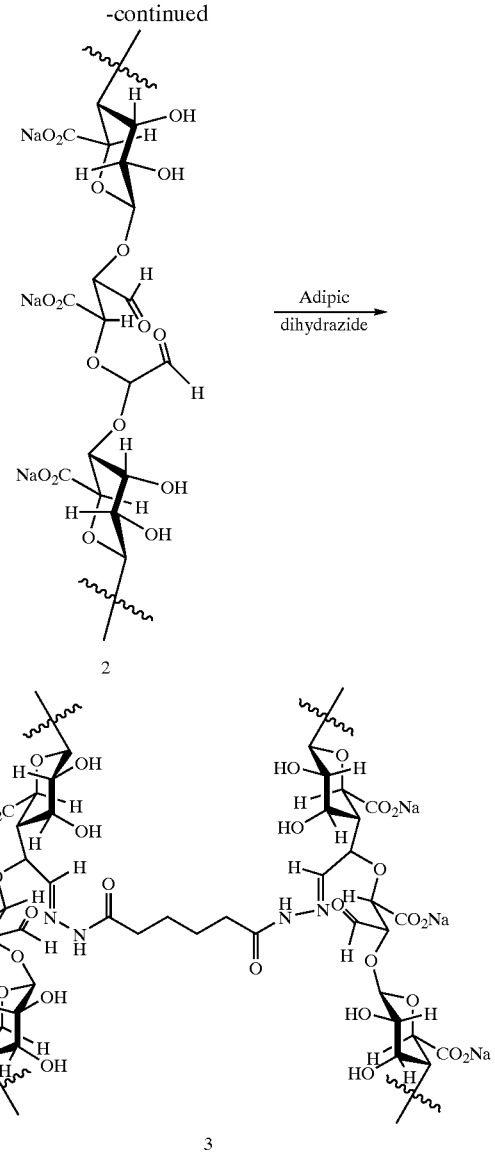

Figure 10:
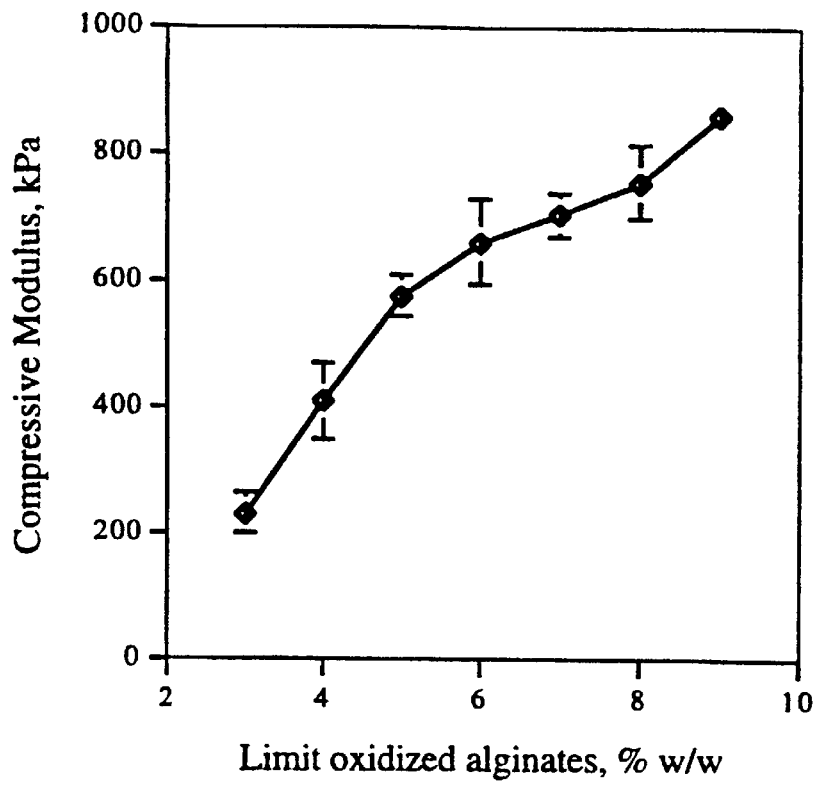
FIG. 10 is a graph showing the compressive modulus of limit-oxidized alginates cross-linked with adipic dihydrazide at various % w/w alginates.

Further, limit-oxidized alginates were cross-linked with adipic dihydrazide at various % w/w alginates. The compressive modulus of the resulting gels was measured and evaluated (FIG. 10). Gelling was set at 3% w/w alginates with a modulus of 200 kPa, and increased with the alginate percentage to reach 900 kPa at 10% w/w alginate content. This cross-linking procedure provides a wide range of control (700 kPa) over the mechanical strength of alginate-based biomaterials.

Figure 11:
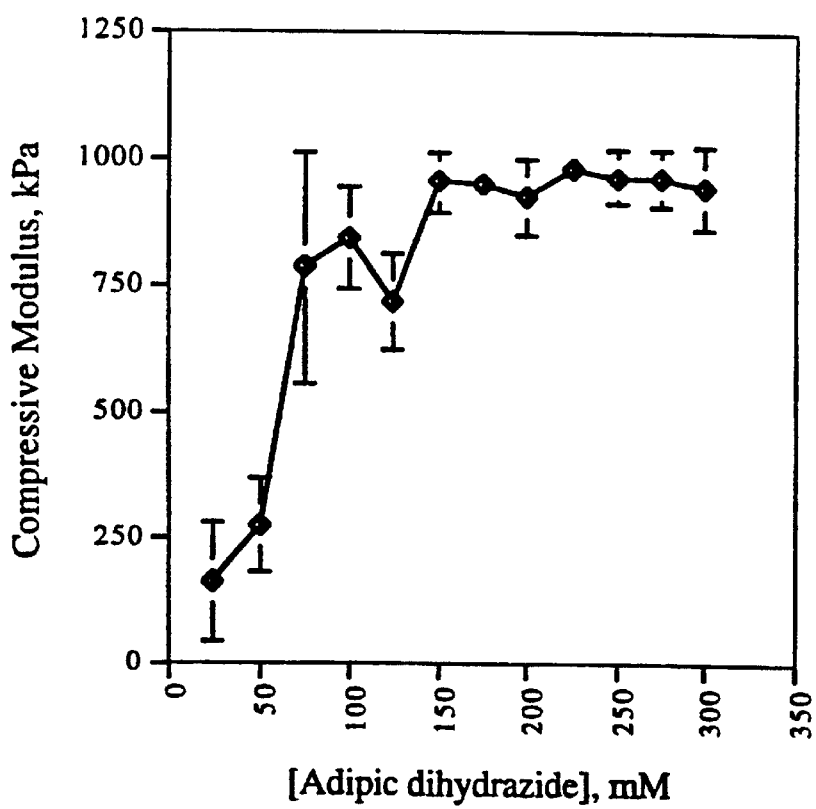
FIG. 11 is a graph showing that the mechanical strength of cross-linked limit-oxidized alginates depends on the concentration of the cross-linker as well as the calcium ion content in the final gel.
Figure 12:
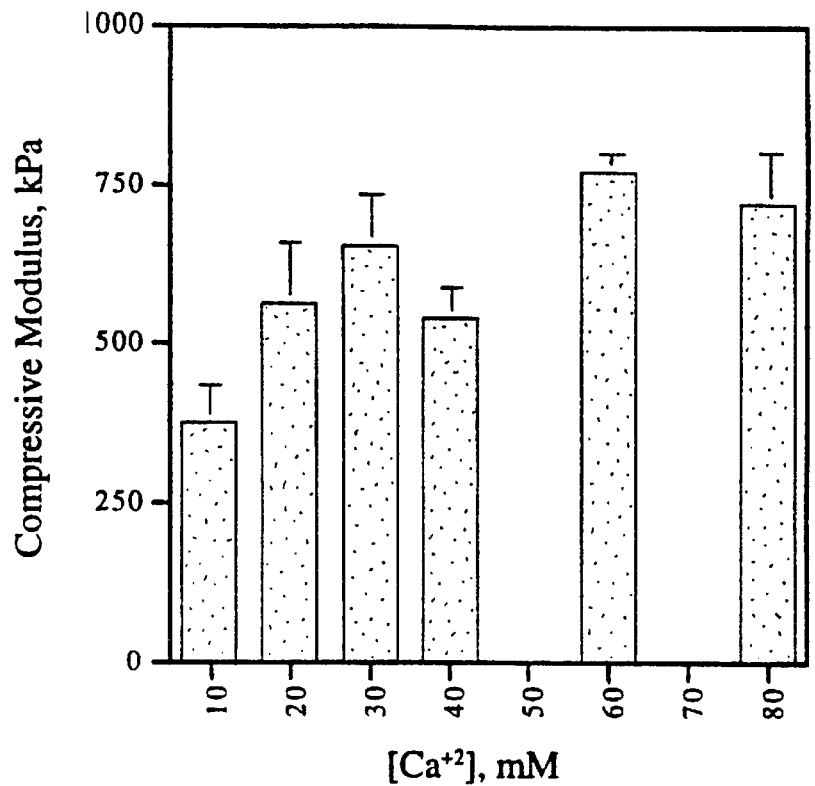
FIG. 12 is a graph showing a significant increase in the compressive modulus as the calcium ion concentration increased.

The mechanical strength of cross-linked limit-oxidized alginates also depended on the concentration of the cross-linker as well as the calcium ion content in the final gel. The compressive modulus increased with the concentration of adipic dihydrazide in the gel (FIG. 11). For example, at 25 mM adipic dihydrazide, the modulus was at 200 kPa and increased to 100 kPa at 150 mM. No difference was observed at higher concentration of the cross-linker. A significant increase of 250 kPa was also observed for the compressive modulus as the calcium ion concentration increased from 10 mM to 30 mM (FIG. 12).

Example 18

The polyguluronate sequence responsible for alginate gelation was isolated, derivatized and cross-linked to form hydrogels, analogous to the scheme shown in Example 17, but for an un-crosslinked material. Thus, sodium polyguluronate, 1, was isolated from alginates by acid hydrolysis following a modified procedure (Haug, A.; Larsen, B.; Smidsrod, O. Acta Chem. Scand. 1966, 20, 183–190; and Haug, A.; Larsen, B.; Smidsrod, O. Acta Chem. Scand. 1967, 21, 691–704). The product was characterized by FTIR, H-NMR, and $^{13}$C-NMR and correlated well with the reported characterizations (see also Penman, A.; Sanderson, G. R. Carbohyd. Res. 1972, 25, 273–282). Sodium polyguluronate was derivatized by sodium periodate oxidation at ambient temperatures to yield polyaldehyde guluronate (PAG), 2. The degree of oxidation was controlled by the mole equivalent periodate used in each reaction. The reaction was monitored by the appearance of the aldehydic symmetric vibrational band (carbonyl) via FTIR. PAG was then cross-linked via the aldehyde groups with adipic dihydrazide to form hydrogels, 3. This process was followed by the disappearance of the symmetric vibrational band at 1735 cm$^{-1}$.

A common approach for the immobilization of molecular probes and proteins onto proteoglycans is the partial periodate oxidation the polysaccharide portion of the proteoglycan followed by coupling via the formation of a Schiff or hydrazone linkage. The same basic approach was utilized to couple a bifunctional cross-linker to partially oxidized sodium polyguluronates. This cross-linking provides an additional level of control, beside ionic cross-linking, over the mechanical stability and strength of the hydrogel under investigation.

Example 19

Figure 13:
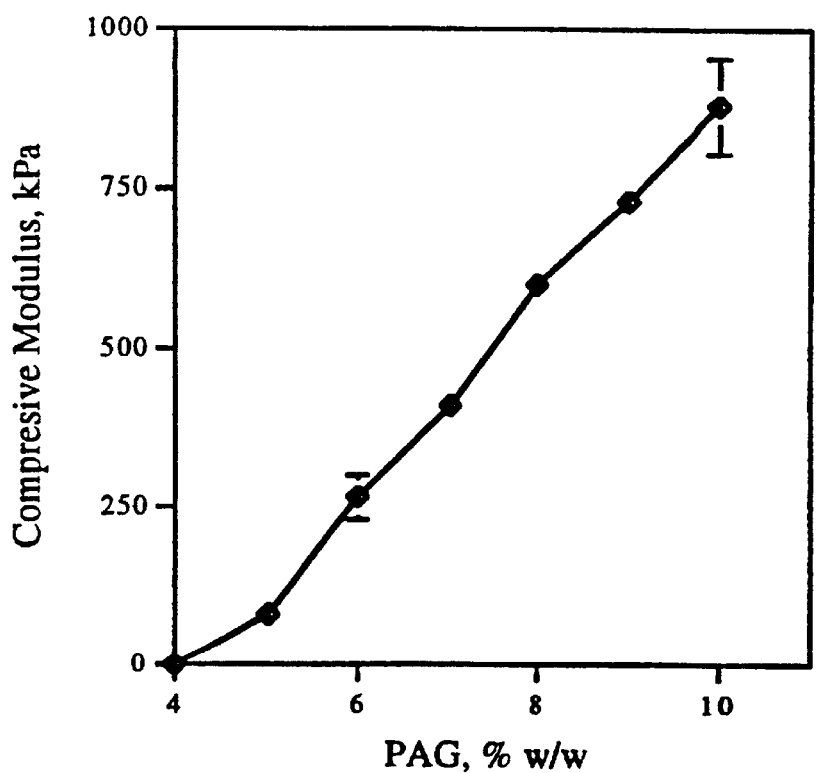
FIG. 13 is a graph for gels cross-linked at various concentrations of polyaldehyde guluronate wherein the compressive modulus was measured and plotted against final % w/w PAG.

To achieve an understanding over the factors behind the gelling properties of certain materials, it was essential to investigate the effect of varying the concentration of polyaldehyde guluronate, adipic dihydrazide, and calcium ions in the resulting gels. Hence, gels were cross-linked at various concentrations of polyaldehyde guluronate and the compressive modulus was measured and plotted against final % w/w PAG (See FIG. 13). Whereas no hydrogels formed with 4% w/w PAG and below, even after 48 hours time interval, cross-linked polyaldehyde guluronate gelled starting at 5% w/w PAG with a compressive modulus of 82 kPa. The compressive modulus then increased as the PAG content in the final gel increased to reach 880 kPa at 10% w/w PAG. This was expected since the number of aldehydic functional groups increased with the PAG content in the gel. Hence, the efficiency of the cross-linker increases and results in a larger modulus. As a result, varying the % w/w PAG in the final gel, can provide a control over the elasticity as well as the strength of the corresponding gel.

Figure 14:
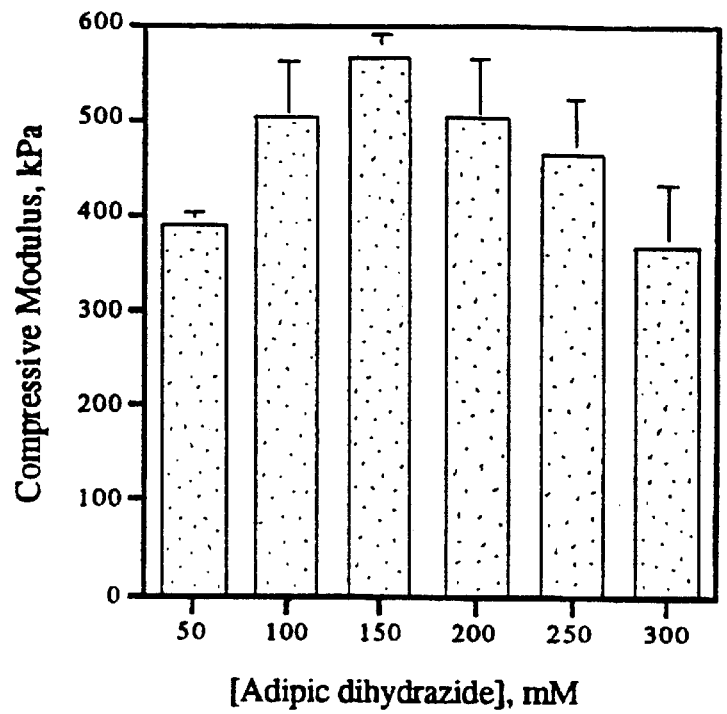
FIG. 14 is a graph of the compressive modulus versus adipic dihydrazide concentration.

The mechanical strength of gels can be increased by increasing the degree of cross-linking. Hence, 6% w/w PAG was cross-linked at different concentrations of adipic dihydrazide and the compressive modulus was evaluated. It was found that increasing the concentration of adipic dihydrazide resulted in an increase in the compressive modulus of 6% w/w PAG. An optimal value of 560 kPa was obtained for the modulus at a concentration of 150 mM adipic dihydrazide. As the concentration of adipic dihydrazide was increased further, the modulus decreased to 350 kPa (See FIG. 14). Theoretically, the efficiency of cross-linking should decrease when the amount of hydrazide functional groups exceed the number of aldehydes in the polymer. In other words, at high adipic dihydrazide concentrations, the cross-linker reacts with only one aldehydic group while the other terminus does not react. As a result, the degree of functional cross-linking will decrease even though that the degree of incorporation of the adipic dihydrazide have also increased.

Figure 15:
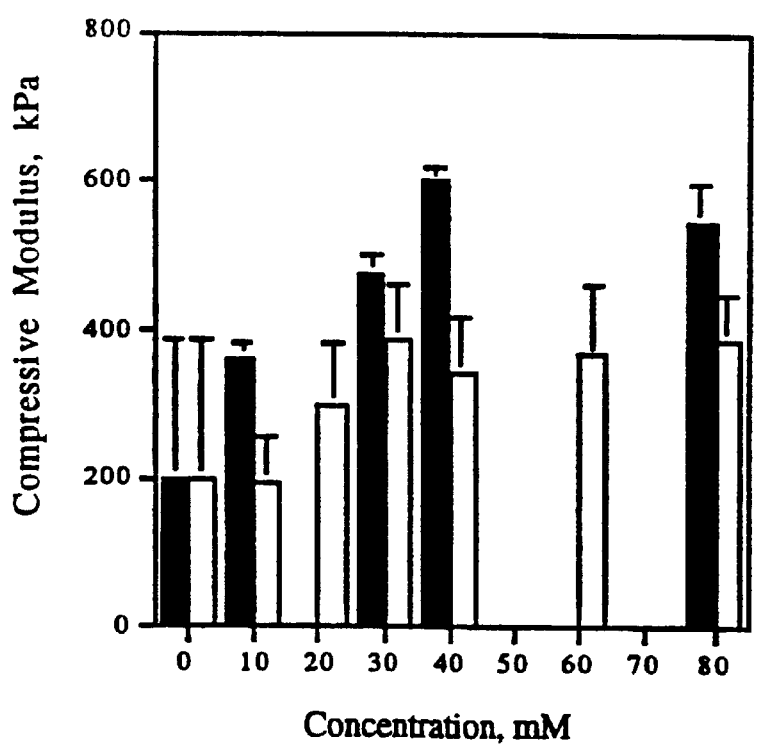
FIG. 15 is a graph showing that the compressive modulus of the gels increased with increasing calcium concentrations.

In comparison to unmodified alginates, cross-linked polyaldehyde guluronates can also be controlled by the amount of calcium ions present in the these materials. PAG (6% w/w) was cross-linked with adipic dihydrazide (150 mM) at various concentrations of calcium and sodium chloride (such as 10, 20, 40, 80, and 100 mM). The compressive modulus of the resulting gels increased with increasing calcium concentrations to an optimal value of 600 kPa at 40 mM calcium chloride (See FIG. 15), wherein the open block, ▢, is sodium chloride and the closed block, ▩, is calcium chloride). Above this concentration, there was no statistical differences in the compressive modulus. This indicates that ionic cross-linking, similar to that in alginates, could provide another level of control over the mechanical properties of these materials. To eliminate the contribution of the ionic strength to the increase in the compressive modulus, PAG was also cross-linked in the presence of sodium chloride at the same concentrations as above. Even though a slight increase in the modulus was observed initially as sodium ions content increased, the value of the modulus leveled out at 390 kPa. There was a significant difference of 210 kPa between the optimal modulus in the presence of calcium and sodium ions. This difference in the compressive modulus (150 kPa) clearly demonstrates that the presence of calcium indeed contributes to the mechanical strength of these materials.

Figure 16:
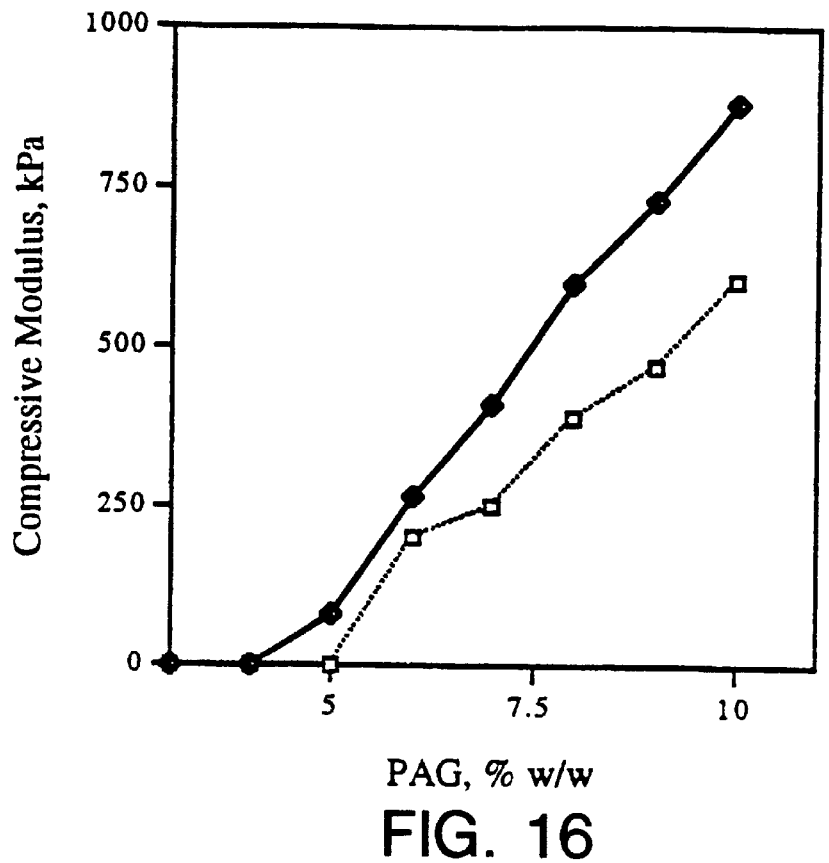
FIG. 16 is a graph showing that by adjusting the pH a change in the compressive modulus was observed.

One potential application for these materials is their use as three dimensional matrices for cell transplantation as mentioned above. Hence, to ensure cell survival and proliferation in these materials, it was necessary to investigate their gelling behavior at physiological conditions (pH 7.4). By adjusting the pH of these materials to 7.4, a slight decrease in the compressive modulus was observed. For example, at a pH of 7.4, no gel was formed at 5% w/w PAG, whereas at lower pH gelling was set starting with 5% w/w PAG (See FIG. 16), wherein the open block, ▢, is at pH 7.4 and the closed block, ▩, is at pH<7). Moreover, the modulus was 600 kPa at 10 % w/w PAG compared to 880 kPa for the original gel condition. This was expected since it is well known that the reactivity of hydrazide groups with aldehydes is optimal at lower pHs. Under acidic conditions, aldehydes are protonated and, hence, are more susceptible to nucleophilic attack by the hydrazide groups. At neutral to basic conditions however, slower kinetics are in effect and a longer time interval is required for the completion of the reaction. This results in a lower degree of cross-linking which directly causes a decrease in the compressive modulus.

The degree of cross-linking in these materials can also be controlled by varying the degree of oxidation of the polyguluronate chains (see Painter, T.; Larsen, B. Carbohyd. Res. 1969, 10, 186–187; Painter, T.; Larsen, B. Acta Chem. Scand. 1970, 24, 813–833; and, Ishak, M. F.; Painter, T. Acta Chem. Scand. 1971, 25, 3875–3877).

Figure 17:
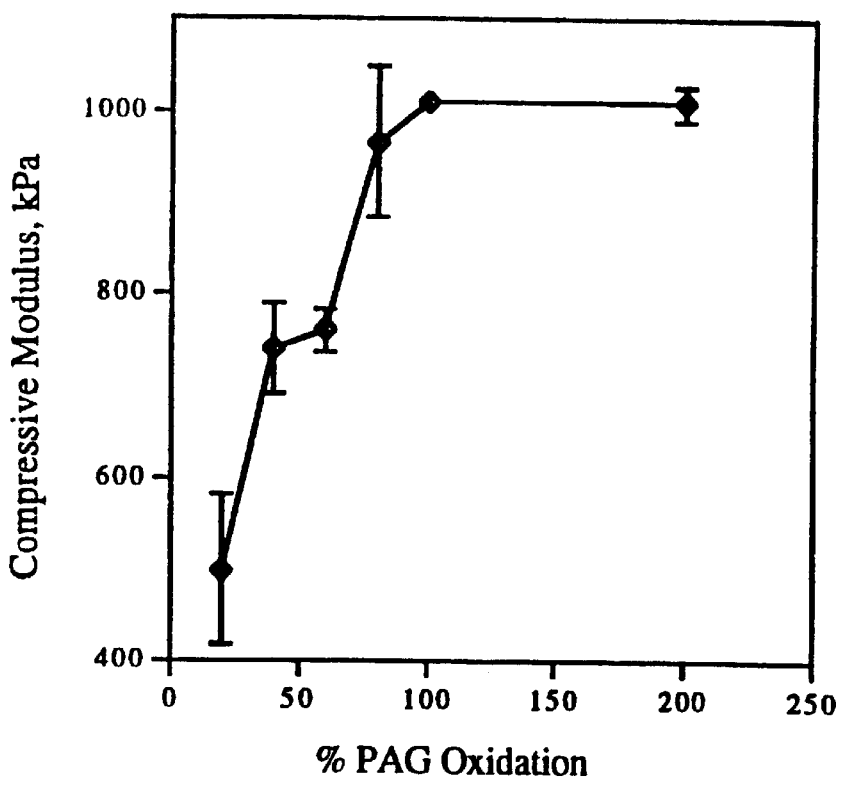
FIG. 17 is a graph showing that the degree of cross-linking in these materials can also be controlled by varying the degree of oxidation of the polyguluronate chains.

This provided another control over the number of aldehydic units on the polyguluronate strand that are available for cross-linking. As a result, polyguluronate was oxidized using various amounts of sodium periodate and cross-linked at 10% w/w PAG with adipic dihydrazide at the optimal concentration of 150 mM in 24 well plates. All materials gelled, starting at 20% theoretical oxidation with a compressive modulus of 500 kPa (See FIG. 17). The modulus increased with the percentage of oxidation of polyguluronate to reach a maximum value of 1000 kPa at 100% theoretical oxidation.

These results clearly indicate that a wide range of mechanical stability could be achieved by varying the degree of oxidation of polyguluronates. Whereas cross-linked 20% oxidized PAG exhibited weak gels comparable with alginates, 80% oxidized PAG and above were stiff and brittle with high compressive moduli. These characteristics are very desirable in processing biomaterials for cell immobilization and as drug delivery systems as well. Depending on the degree of oxidation of the polymer, devices with specific pore sizes and mechanical strength can be provided to deliver cells or therapeutic drugs to the site of implantation.

Example 20

A critical question, in terms of cell transplantation, is whether cells present in the un-crosslinked monomers will be harmed by the cross-linking reaction. Smooth muscle cells (rat aorta-derived) were placed into a PAG solution, and then cross-linking via addition of adipic acid dihydrazide. Incorporation of the smooth muscle cells within the gels was approximately 100%, and the cell number and metabolic activity of the cells was maintained for the 7 days of the experiment. These results indicate that cells can be transplanted in materials cross-linked with this chemistry (PAA polymers also utilize same cross-linking). We did not expect cells to proliferate in these matrices, as they do not contain cell adhesion ligands, and we did not observe any proliferation. RGD-containing and other cell adhesion peptides can be readily coupled to these polymers as described above to enhance the cell interaction. Coupling efficiencies of approximately 70% have been achieved using the coupling chemistry optimized for alginate.

Example 21

Figure 18:
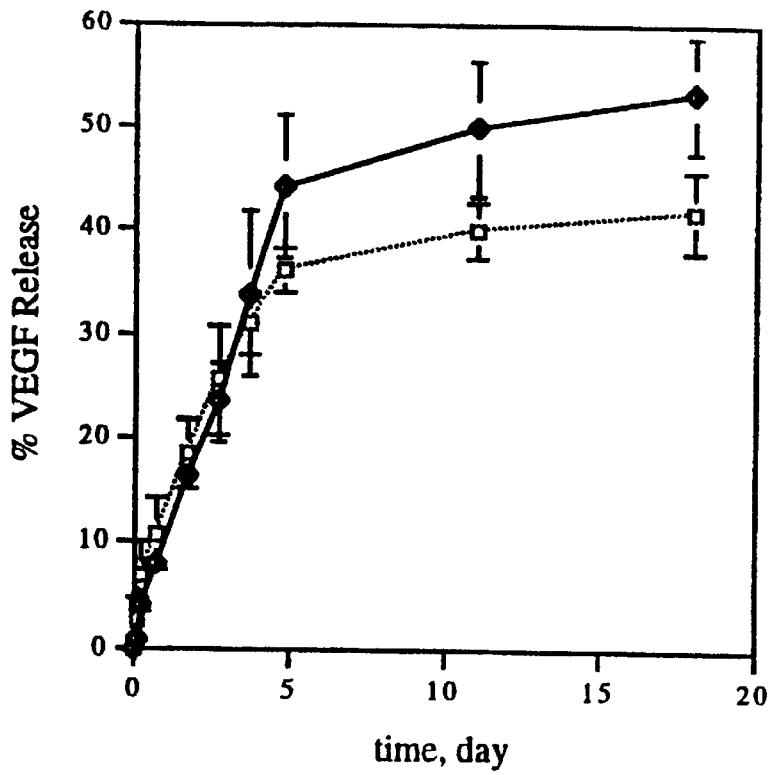
FIG. 18 is a graph of the % of VEGF release over time.

The suitability of these polymers as delivery vehicles for angiogenic factors was also investigated. VEGF was mixed with the PAG, and then the PAG was cross-linked. VEGF release was monitored by adding trace amounts of $^{125}$I-VEGF. PAG (20% w/w) was cross-linked with adipic dihydrazide containing $^{125}$I-labelled VEGF in the presence of calcium chloride, and mixture was allowed to gel for one hour and then incubated at 37° C. in DMEM medium. The medium was replaced with fresh medium and counted for its radioactivity. Little to no burst release of the VEGF was observed in any of the experimental conditions (See FIG. 18), wherein the open block, ☐, is with heparin and the closed block, ■, is without heparin). In the presence of heparin, the VEGF was released at a rate of 7% total incorporated growth factor/day for 5 days, then a slower release of 2%/day for the next 14 days. In the absence of heparin, a higher initial release of 9%/day for 5 days was observed, followed again by a slower release of 2%/day for the next 14 days.

Example 22

Figure 19:
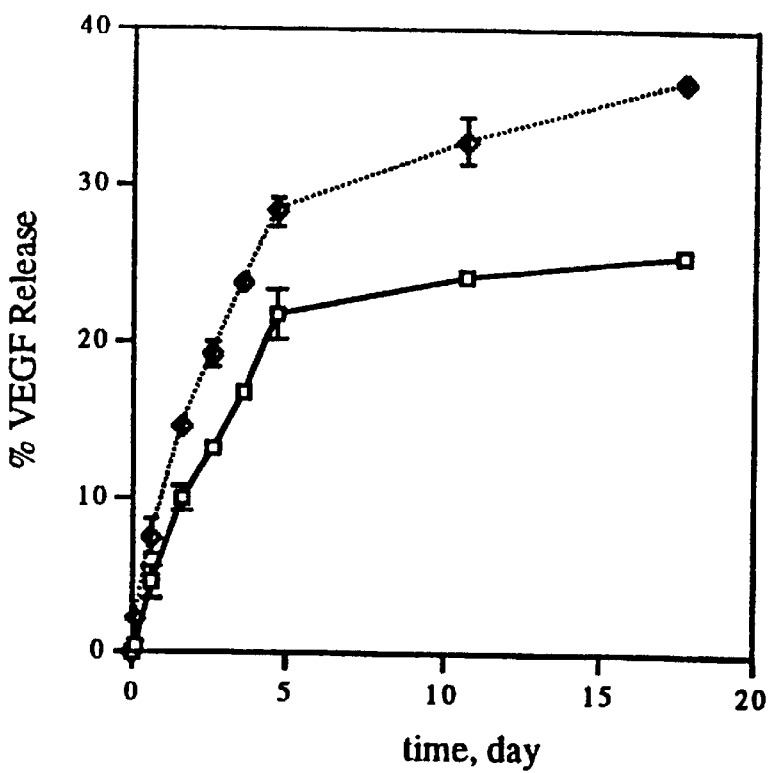
FIG. 19 is a graph of the % of VEGF release over time for a different system.

Polyaldehyde guluronate was also cross-linked with adipic dihydrazide in the absence of calcium chloride at 10% w/w PAG. A slower release of $^{125}$I-VEGF from these materials was observed in both cases, with and with out heparin. In the presence of heparin, VEGF was initially released at a rate of 4%/day for 5 days, followed by a slower release at a rate of 0.2%/day for 14 days (See FIG. 19), wherein the open block, ☐, is with heparin and the closed block, ■, is without heparin). In the absence of heparin, VEGF was released at a rate of 6%/day for five days, followed by 0.8%/day for the next 14 days. These experiments suggest that it is possible to control the rate at which VEGF is released from these materials by controlling the presence of calcium and heparin. We anticipate that the release will be strongly dependent on the PAG concentration and cross-link density as these variables will regulate the pore size in the hydrogel. It is possible to achieve release rates over a very wide range by altering these variables.

Example 23

Figure 20:
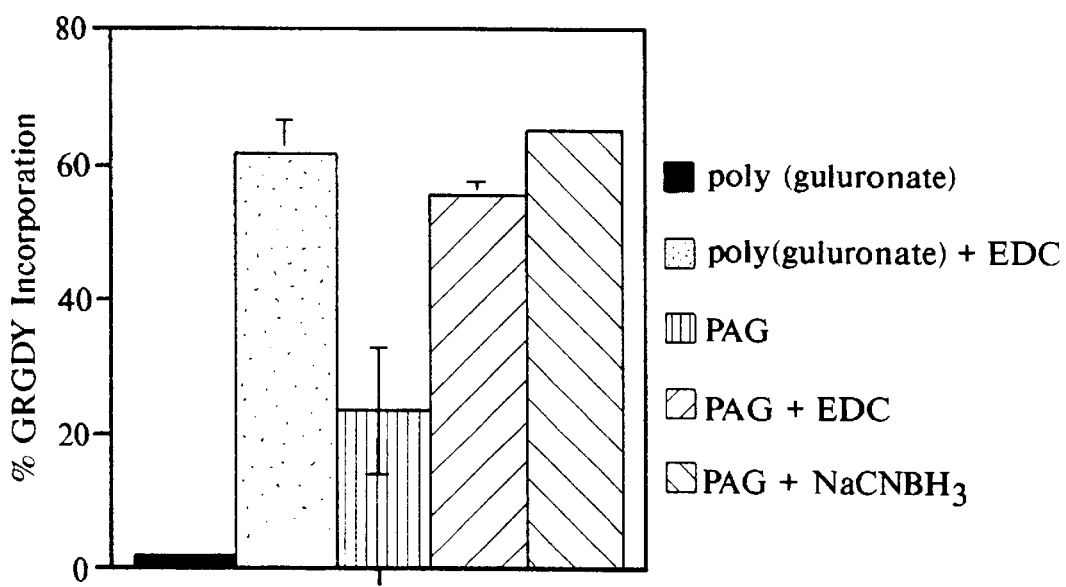
FIG. 20 shows the degree of coupling for certain species.

A cell adhesion ligand, GRGDY, was coupled to sodium poly(guluronate) and PAG with the same type of EDC chemistry utilized for coupling to alginate. To monitor the degree of coupling, trace $^{125}$I-GRGDY was mixed with the adhesion peptide and the mixture was dialyzed against double distilled water. The dialyzate was counted in a liquid scintillation counter to determine the amount of radioactive material present. In the absence of EDC, only 1.5% GRGDY was present in sodium poly(puluronate), whereas, in the presence of EDC, 61% peptide was incorporated (See FIG. 20). In PAG material, 55% GRGDY was incorporated with EDC compared to 24% in the absence of EDC.

Different chemistry can also be used to couple this ligand to PAG. This approach utilizes the reductive amination coupling of the amine functional groups on the terminus of the peptide and the aldehydic group abundant in the PAG material. Essentially, the amine reacted with the aldehyde to form a labile imine bond which was reduced using sodium cyanoborohydride (NaCNBH$_3$) to form a stable amine linkage. The degree of incorporation of the peptide into the PAG material was 65%. The imine bond between the amino terminal of the peptide and the aldehyde group of PAG formed with this reaction is likely also forming when the EDC chemistry is utilized to couple the peptide. This reaction ties up some of the peptides and prevents them from reacting with the activated carboxylic acid groups, hence, resulting in a lower degree of incorporation of the peptide (55%). The same reaction essentially explains the reason behind the incorporation of the peptide in the absence of any additive (24%).

This new coupling chemistry can also be used to chemically bind other peptides and proteins (e.g., growth factors) or drugs to PAG and limit-oxidized alginates. Importantly, this reaction results in the formation of a labile bond that will degrade and release the bound molecule. This will allow drugs to be released slowly from the matrices, and this release will be chemically controlled, diffusion controlled or controlled by both processes. This bond can be easily reduced using sodium cyanoborohydride to yield a very stable bond if one wishes the bound molecule to remain bound (e.g., cell adhesion ligand). Any growth factor having pendant amino groups can be coupled with this reaction. Pharmaceutical drugs that could potentially be used will have amino groups available from the imine bond formation according to the scheme below for example. In addition to the amine group, growth hormones and drugs could be modified to incorporate free hydrazines, hydrazides, or semicarbazides groups that can form hydrazone or semicarbazone linkages respectively. This will allow for a different release of the drug or hormone and consequently provide another level of control over the rate of release.

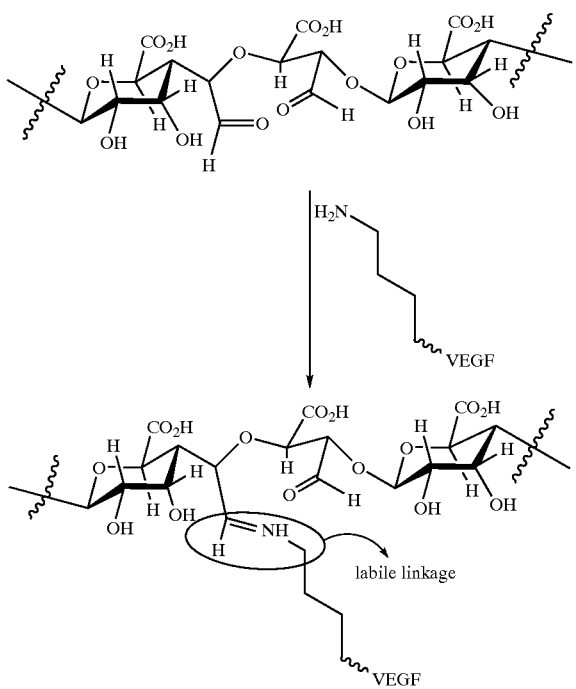

Incorporation of VEGF in limit oxidized alginates and PAG matrices

Example 24

PEG hydrazide cross-linkers. PAG can be crosslinked with adipic acid dihydrazide. Dihydrazide cross-linkers can be synthesized with various lengths starting with a polyethylene glycol core. Poly(ethylene glycol), PEG, with molecular weights of 200, 400, 1000, and 3400 can be reacted with succinic anhydride in the presence of N,N-dimethylamino pyridine to form poly(ethylene glycol) disuccinate)

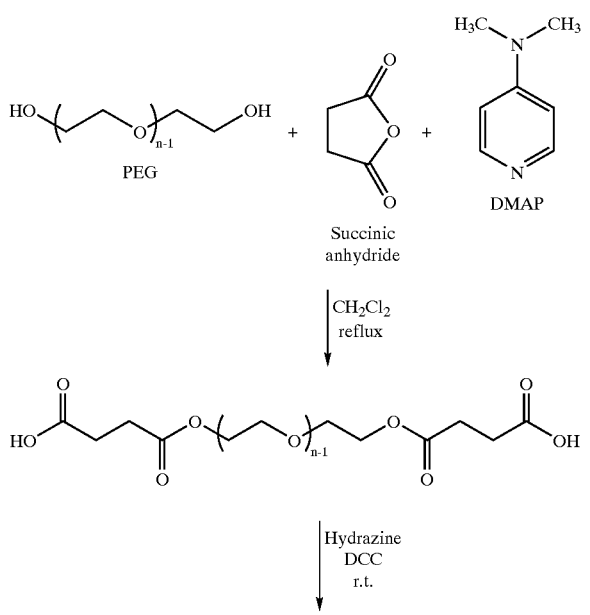

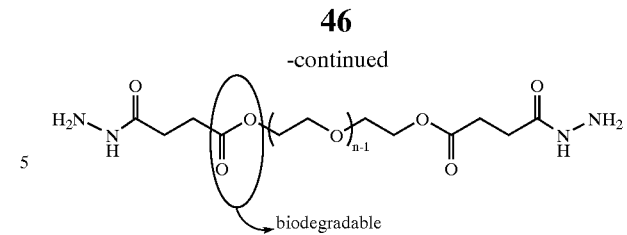

The ester bonds formed between the PEG core and the succinate groups are biodegradable. Hydrazine, can then be coupled to the terminals of these polymers using DCC chemistry to yield polyethylene glycol dihydrazides. By starting with PEGs with different molecular weights, dihydrazide cross-linkers with various chain lengths can be synthesized. These polymers can be used to cross-link poly(aldehyde guluronates), PAG.

Example 25

To gain more control over the degradability of PAG materials, a method to synthesize cross-linkers with nondegradable cores is provided. Reacting PEG with different molecular weights with methyl chloroacetates will form dicarboxymethyl-PEG which will then be coupled to hydrazine at both terminals to yield PEG dihydrazide.

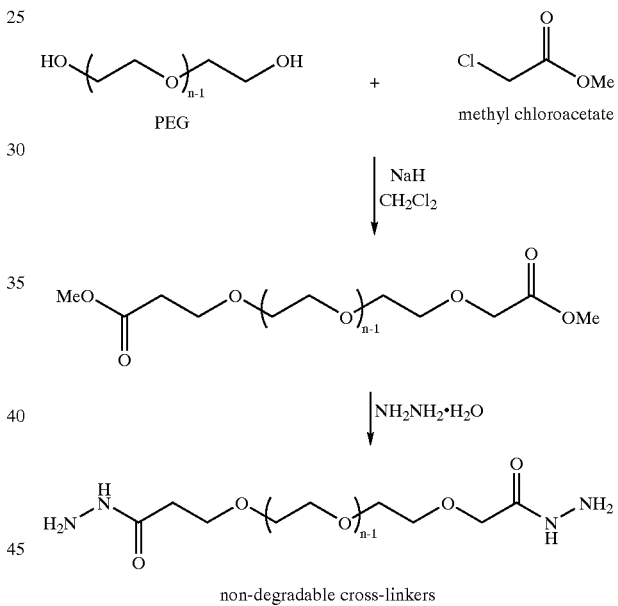

These dihydrazides have a non-degradable core with ether linkages. As before, controlling the molecular weights of the starting PEG polymers will yield PEG dihydrazides with various chain lengths.

These dihydrazides can be used to cross-link PAG and form materials with only one degradable linkage which is the hydrazone bond. This bond can be further stabilized by borohydride reduction to yield nondegradable materials. Hence, PAG polymers can be crosslinked with dihydrazides to form non-degradable materials, materials with hydrazone degradable bonds, or materials with hydrazone and ester bonds both of which are degradable. This approach will provide materials with various rates of degradation. Moreover, by selecting the appropriate length of PEG polymers used the mechanical properties of the resulting cross-linked biomaterial can be controlled.

Example 26

A photopolymerizable polyguluronate can be synthesized from hydrazido acrylate monomers coupled to G-block polyguluronate via the aldehydic terminus. These materials can then be injected into the desired site and polymerized photochemically to form hydrogels. Hydrazido acrylate can be synthesized starting with acryloyl chloride and t-butylcarbazate to form the protected hydrazido acrylate.

ethyl ammonium chloride in aqueous solutions using ammonium persulfate as the initiator provides G-block incorporated polymers with various rigid backbone structures.

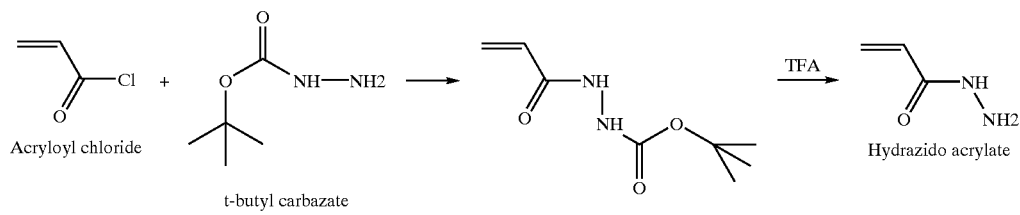

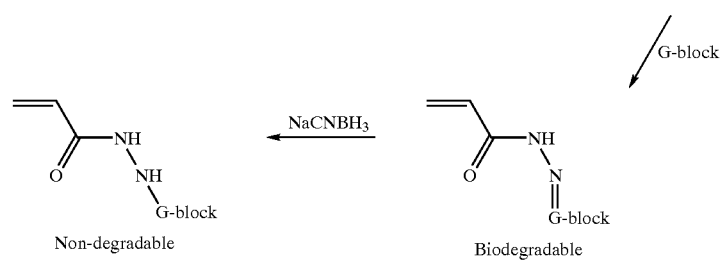

Deprotection using trifluoro acetic acid, TFA, will afford the desired monomer. This methodology provides a means to deliver G-block into the desired site and polymerize it afterwards via photoinduced free-radical polymerization. Hydrazides react with aldehydes as in the case of PAG. In this example, the hydrazides react with the hemiacetal terminal of G-block to form an acrylic hydrazone terminal on the G-block chain. Hydrazido acrylates were chosen because of the ease of incorporating these functional groups in G-blocks.

These materials could be prepolymerized into the desired shape and used as three-dimensional matrices for cell transplantation, or alternatively mixed with cells and injected as solutions into the implantation site. Photoinduced free-radical polymerization of the acrylate groups would then provide a non-degradable backbone.

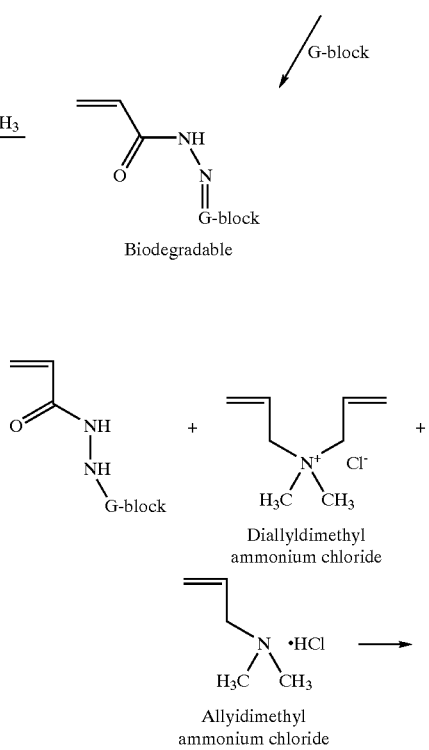

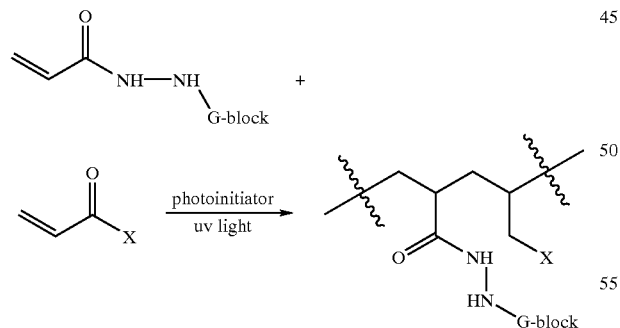

These monomers can be copolymerized with acrylic acid, acrylamide, MMA, HEMA, HPMA, allyl amine, dimethylallyl amine, or other monomers with similar functionality. The degree of G-block incorporation can be controlled by varying the percentages of co-monomer used.

Example 27

Copolymerizing G-block hydrazido acrylates with diallyldimethyl ammonium chloride monomers and allyldim- The pyrrolidine unit formed after the polymerization restricts the mobility of the polymer due to its cyclic structure and renders the backbone more rigid. The stiffness of the backbone is then controlled by the percentage of diallyldimethyl ammonium chloride units incorporated.

Another approach for the synthesis of these polymers is to prepolymerize hydrazido acrylates with diallyl dimethyl ammonium chloride and allyldimethyl ammonium chloride monomers.

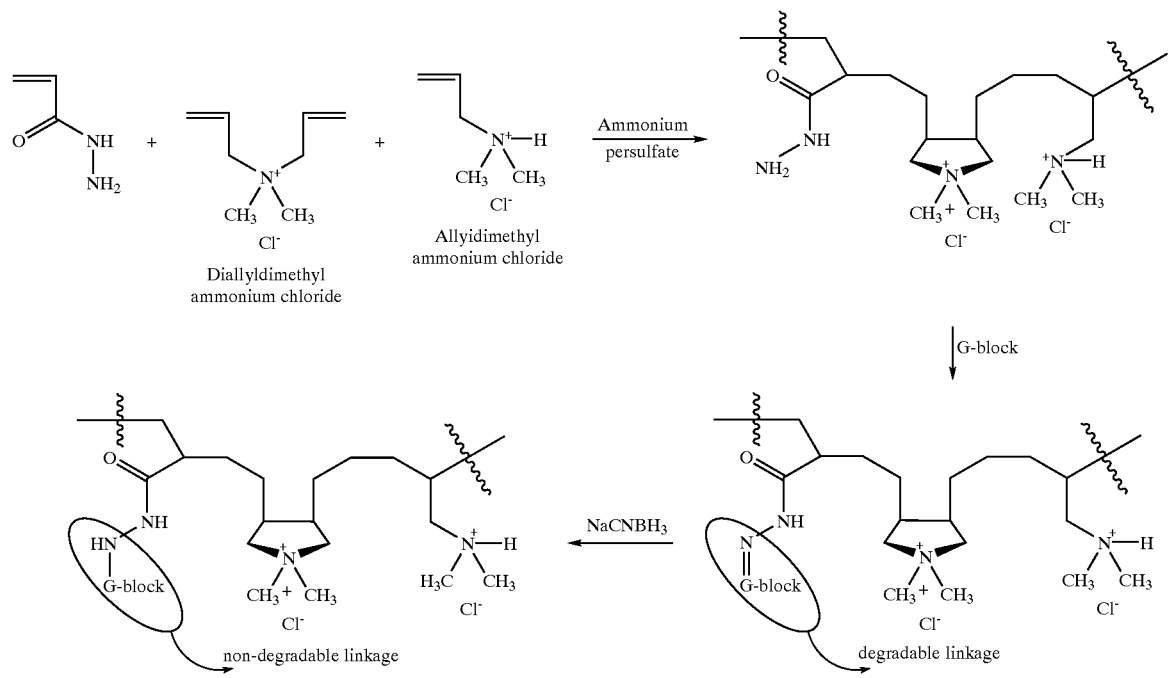

The polymerization is accomplished using ammonium persulfate in aqueous solutions. Afterwards, G-block is coupled to the hydrazido groups to form degradable hydrazone linkages. The hydrazone bond can then be reduced with sodium cyanoborohydride to form the more stable hydrazide linkages.

Example 28

A common approach to control the mechanical strength of poly acrylates and derivatives is by cross-linking these polymers With acrylate-based cross-linkers (Naghash et al., Polymer, 1187–1196, 1997; Dietz and Peppas, Polymer, 3767–3781, 1997). Ethyleneglycol dimethacrylate, hexaethyleneglycol dimethacrylate, and other bifunctional and multifunctional cross-linkers can crosslink G-block-hydrazido acrylate monomers.

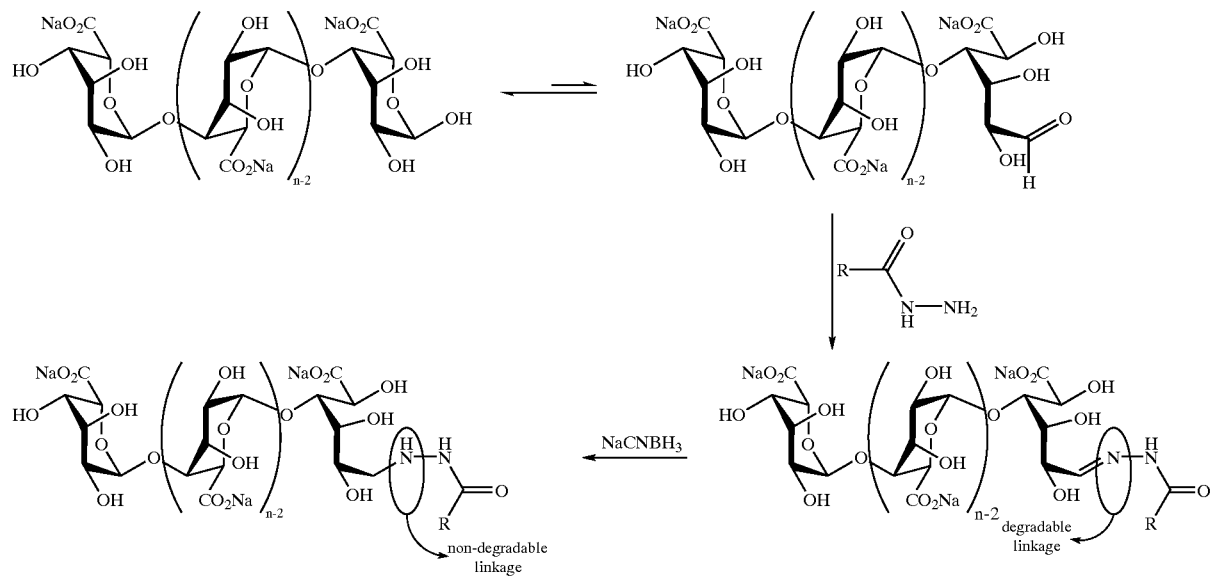

Again, by controlling the percentage of cross-linker in the final product. we can control the mechanical properties of the resulting polymers.

Example 29

Dendritic polymers can be provided by coupling of G-block to PEG-lysine dendritic polymers. It is well known that the hemiacetal terminus of monosaccharides and polysaccharides is in equilibrium with the open aldehyde form.

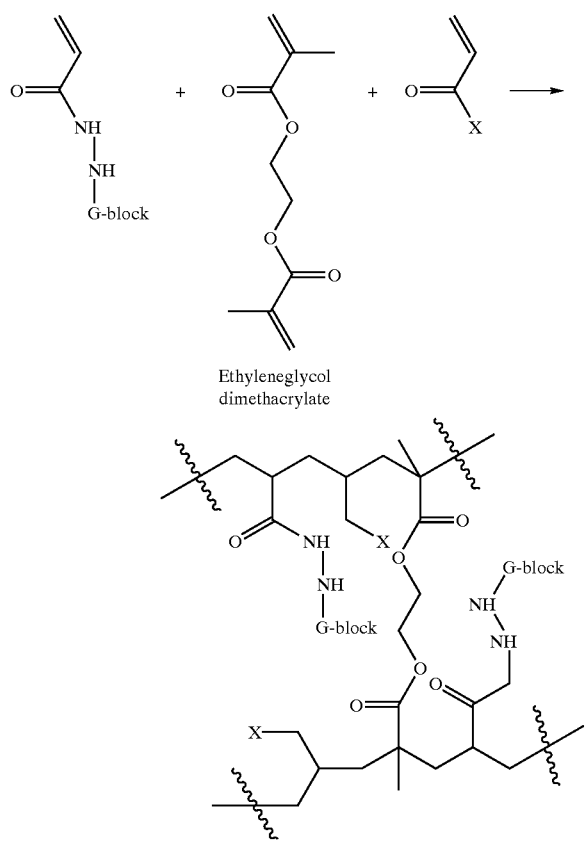

Moreover, the reaction of amines with aldehydes is also in an equilibrium. In the presence of sodium cyanoborohydride, the imine bond formed between the amine arid the aldehyde is reduced which shifts the equilibrium to form more aldehydes and drive the reaction to completion. This process is sluggish, however, and a faster and more efficient method is needed to couple G-block to different polymers. Thus, hydrazide functional groups can be used to achieve this coupling. Hydrazines, hydrazides, and semicarbazides react with aldehydes to form imine-like bonds. This process does not depend on the presence of borohydrides. Hydrazide moieties are more nucleophilic than amines and can attack electrophilic centers like carbonyl groups much faster. In addition, sodium cyanoborohydride could eventually be used later to induce stability on the hydrazone or semicarbazone linkage.

Example 30

Dendrimers with reactive functional groups on the terminals for G-block coupling can be synthesized using a similar method to the one used for lysine dendrimers and the end groups modified to semicarbazide terminals.

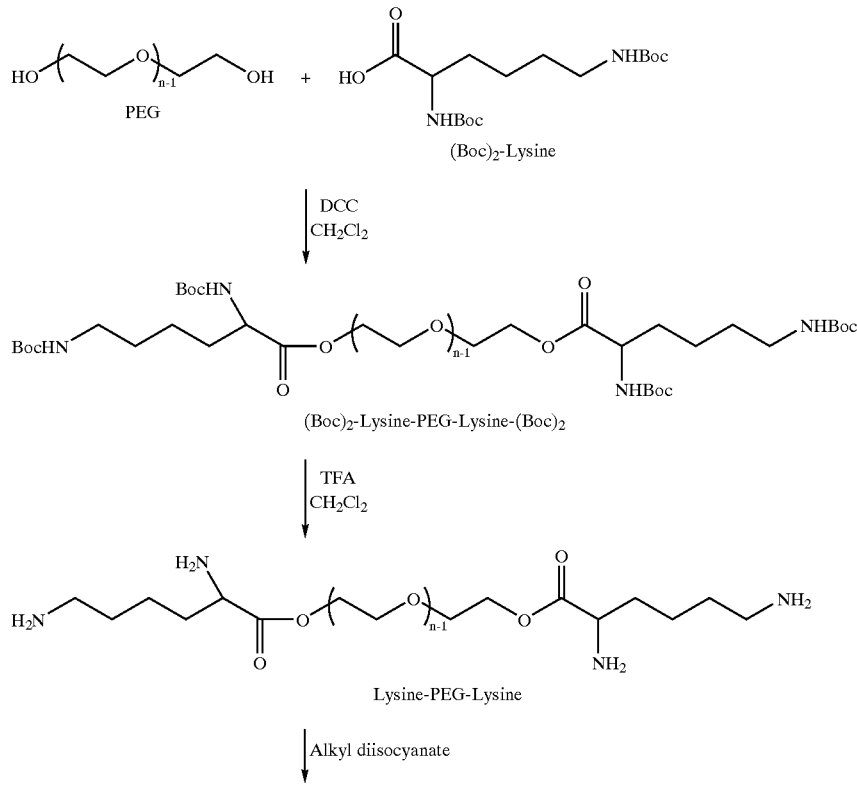

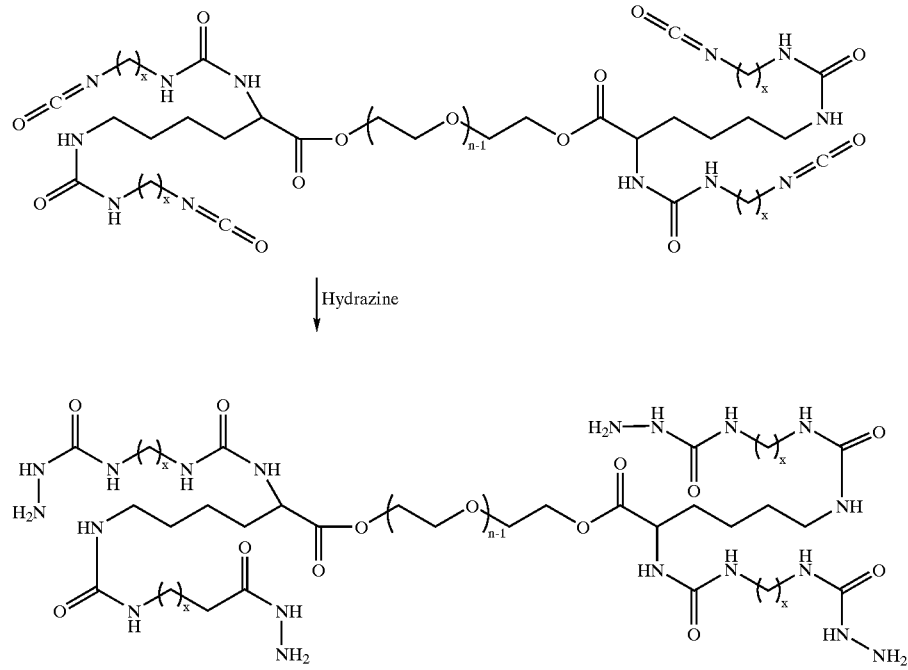

As before, we start with polyethylene glycol, PEG, and couple it to (Boc)2-lysine via DCC chemistry, and deprotect with trifluoro acetic acid, TFA, to form PEG dilysinate. Allowing the PEG dilysinate to react with excess alkyl diisocyanate will provide polymers with an isocyanate group on the terminals. Reacting the isocyanate groups with hydrazine will finally afford the modified dendrimer with four semicarbazide groups available to couple G-block. The same methodology can essentially be used to synthesize PEG hexalysinate, PEG octalysinate, and so on.

Example 31

Comb polymers. Monosaccharides and oligosaccharides have been successfully incorporated into the backbone of polyacrylamides (Calistrom and Bednarski, *MRS Bulletin*: 54–59, 1992). Similar methodologies can be used to incorporate G-block into the backbone of several synthetic polymers. Three methodologies are followed for the syntheses of new biomaterials. The first is by utilizing a poly(vinyl alcohol) backbone functionalized with hydrazido groups onto which G-block chains are coupled. The second method utilizes poly(allylamine) backbones which are also modified to incorporate reactive hydrazido groups for G-block coupling. These backbones are chosen because they are biocompatible and are easily excreted by the kidney with molecular weights of 10,000 or less. The third approach involves coupling polyguluronate to polyaldehyde guluronate. This will result in the formation of a polymer comprised completely of alginate derived molecules.

PVA-based Materials

Low molecular weight poly(vinyl alcohol), PVA, can be modified by reaction with succinic anhydride in the presence of N,N-dimethyl aminopyridine, DMAP, to afford poly(vinylsuccinate) intermediate.

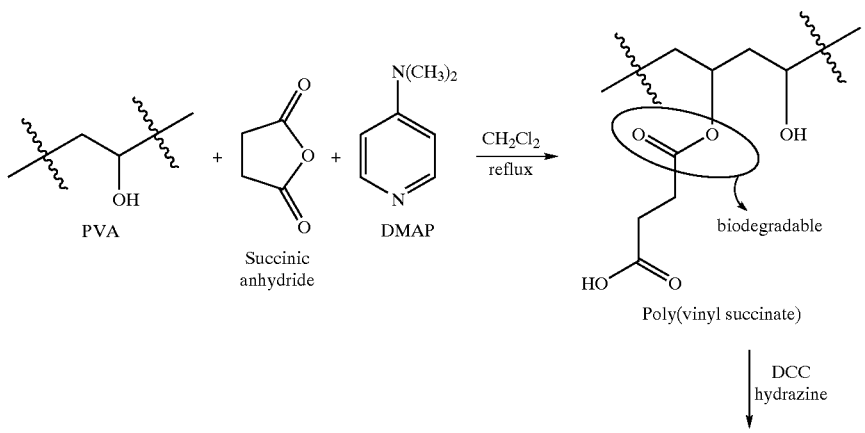

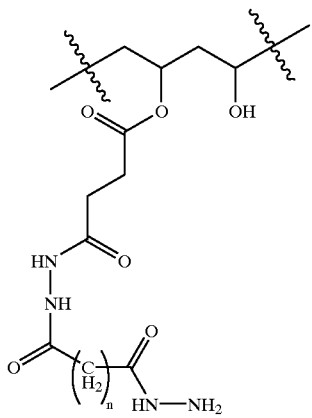

Poly(vinyl dihydrazidosuccinate)

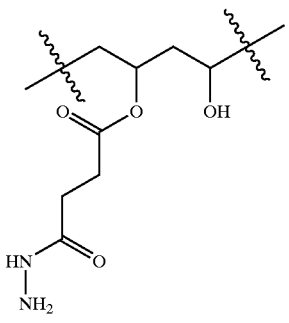

Poly(vinyl hydrazidosuccinate)

The ester bond thus formed between PVA and the succinate group is a biodegradable bond susceptible to enzymatic cleavages in biological systems. Hydrazine, can then be coupled to this intermediate via DCC coupling to form poly(vinylhydrazidosuccinate). Therefore, the degree of hydrazide incorporation can be controlled in the final product by controlling the number of succinic anhydride molecules used in the previous reaction. The control over the degree of hydrazide incorporation is crucial since this will dictate the degree of G-block incorporation in the next step.

Other hydrazide groups which can be incorporated in the PVA backbone are oxalyl dihydrazide (n=0), malonic dihydrazide (n=1), succinic dihydrazide (n =2), adipic dihydrazide (n=4), suberic dihydrazide (n=6), and others. These dihydrazides will provide various lengths for the spacer arms to be incorporated between the PVA backbone and the G-block chains.

Due to the reactivity of hydrazides toward aldehydic groups, the same approach can be used to attach G-block chains to this polymer via the hemiacetal terminus. This provides a synthetic backbone polymer onto which G-block is linked via a degradable linkage.

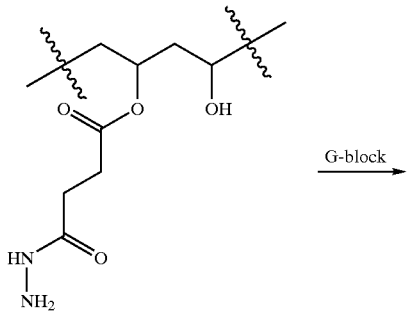

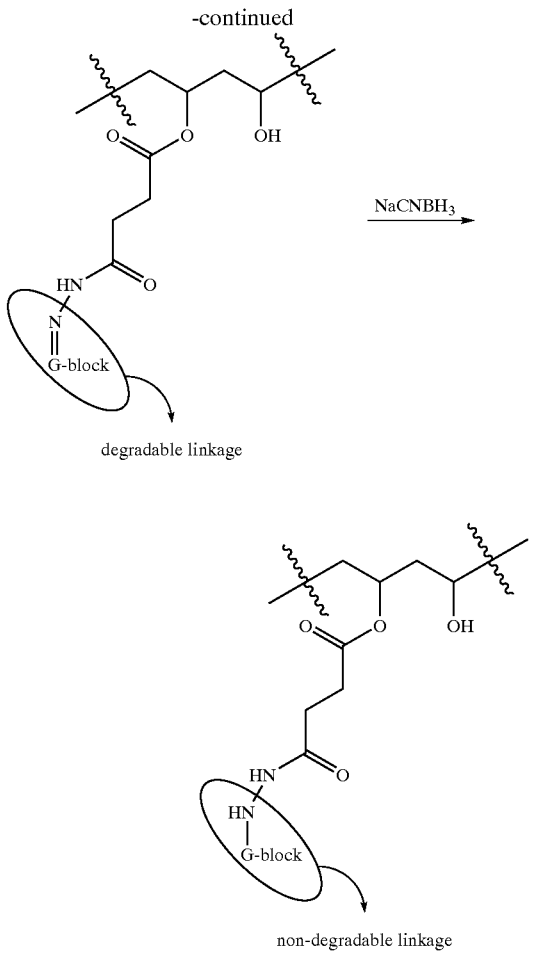

degradable linkage non-degradable linkage

This linkage can be further stabilized by reduction with sodium cyanoborohydride. The degree of G-block incorporation in the final material will exhibit a direct relationship with the gelling properties as well as the strength of the hydrogel formed.

Poly(allylamine)-based Materials

A similar approach is to be used for the modification of poly(allylamine) by reacting it with succinic anhydride followed by hydrazide incorporation using carbodiimide chemistry to form poly(N-allylsuccinamidohydrazides).

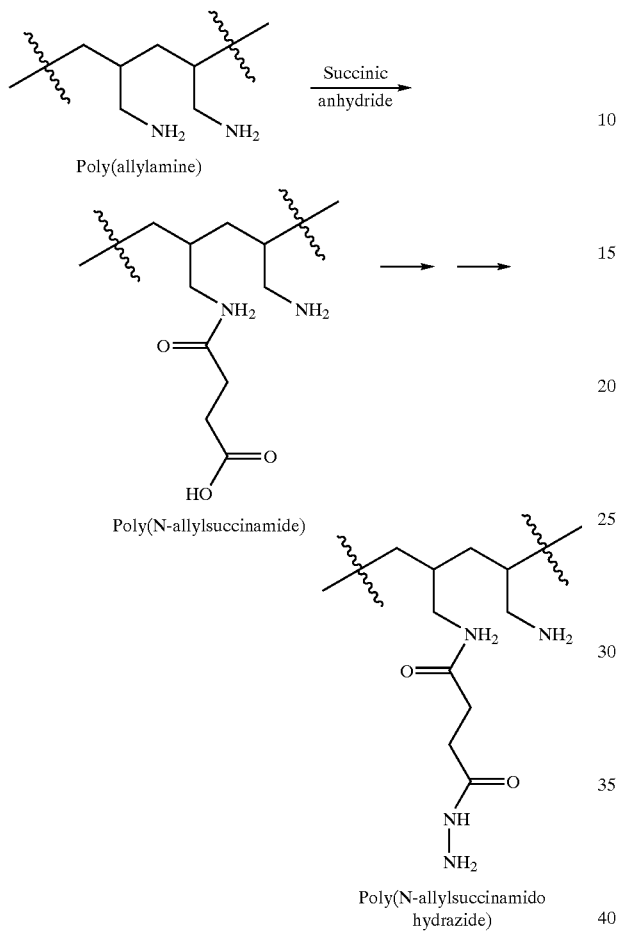

As in the previous example, the reactive hydrazido groups provide a means to attach G-block to the polymer backbone via the hemiacetal terminus. In contrast to the PVA-based materials, the amide bond formed between the poly(allylamine) and the succinate group is a non-degradable bond.

The coupling of G-blocks to both polymer backbones will form biodegradable linkages in the form of hydrazones.

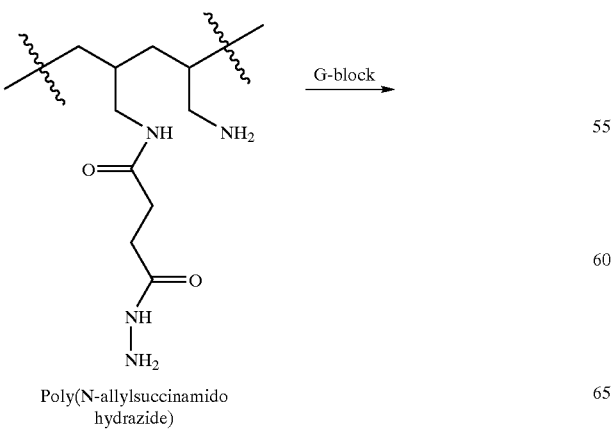

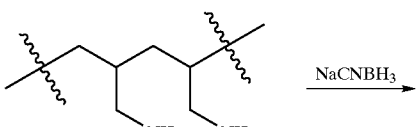

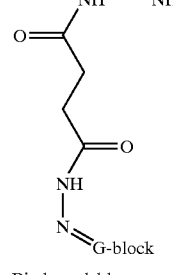

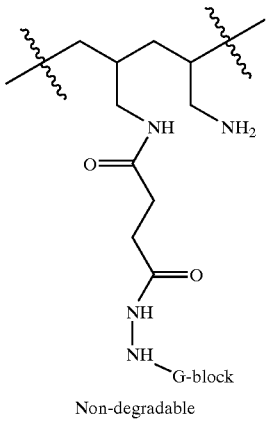

These linkages can be further reduced with sodium cyanoborohydride to form a more stable hydrazine linkage that is non-degradable. It is therefore possible to tailor biomaterials with varying rates of degradation depending on the synthetic methodology followed.

PA G-based Comb Polymers

Polyaldehyde guluronate, PAG, was allowed to react with hydrazine and sodium borohydride to afford the polyhydrazino guluronate derivative. The hydrazine groups on this alginate derived polymer are used to incorporate G-block chains via their hemiacetal termini.

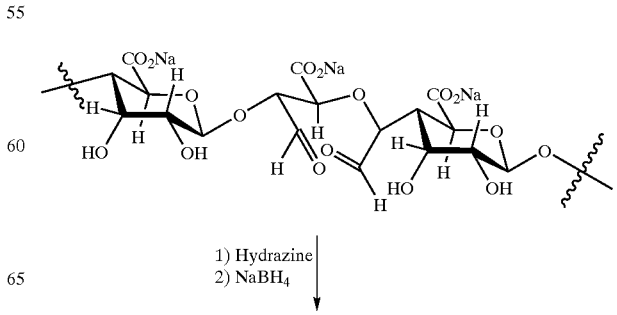

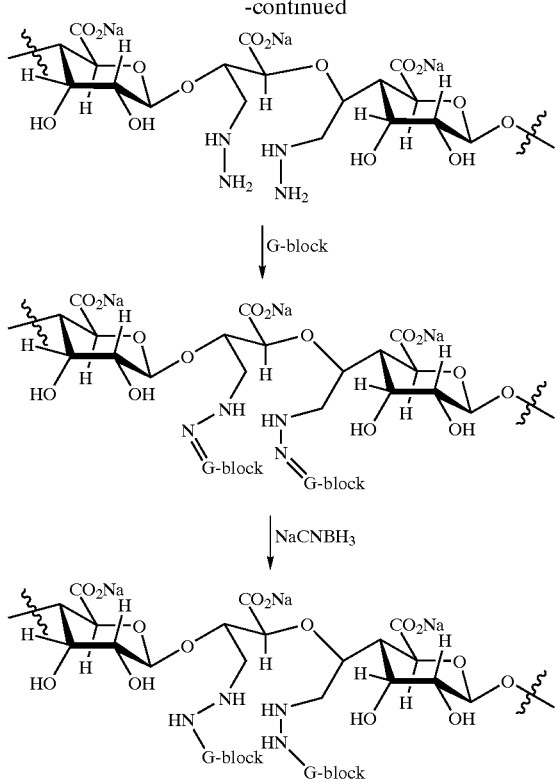

This will provide biocompatible and biodegradable materials from naturally derived polysaccharides with hydrolyzable hydrazone linkages. Hydrolysis of the hydrazone linkage in these materials will lead to short chain polysaccharides that can be excreted by the kidney. Furthermore, reduction of the hydrazone bond by borohydrides can form a chemically stable hydrazine bond that provide non-degradable materials. This will again provide both biodegradable and non-degradable biomaterials derived from natural polysaccharides.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A modified alginate, which comprises at least one alginate chain section to which is bonded by covalent bonding at least one cell attachment peptide or RGD peptide which promotes cell adhesion and growth.

2. The modified alginate of claim 1, wherein the molecule useful for cell adhesion and growth is bonded through a uronic acid residue on the alginate chain section.

3. The modified alginate of claim 1, wherein the alginate chain section comprises an oligomeric block unit of D-mannuronate, an oligomeric block unit of L-guluronate, an oligomeric block unit of D-mannuronate and L-guluronate or a mixture of said block units.

4. The modified alginate of claim 1, wherein the alginate chain section has a molecular weight of less than about 50,000.

5. The modified alginate of claim 1, wherein the alginate chain section has a molecular weight of less than about 30,000.

6. The modified alginate of claim 1, wherein the alginate chain section has a molecular weight of about 100,000 or more.

7. The modified alginate of claim 1, wherein the alginate chain section is a naturally occurring alginate.

8. A modified alpinate of claim 1, wherein the modified alginate contains at least one alginate chain sectiononded to a polymeric backbone section or at least one alginate chain section crosslinked to another alginate chain section on the same or a different molecule.

9. A method for cell transplantation into a system which comprises implanting a modified alginate of claim 8 in a matrix form into the system and subsequently introducing the cells for transplantation into the matrix.

10. A method for treating a human or animal which comprises administering thereto a modified alginte of claim 8, as a matrix for bone or soft tissue replacement.

11. A method for drug delivery which comprises administering to a human or animal a modified alginate of claim 1, wherein the molecule useful for cellular adhesion and growth is a drug and it is bonded to the at least one alginate chain section by a biodegradeable bond.

12. An aqueous composition containing an alginate material of claim 1 and water.

13. An injectable solution for forming cell transplantation matrices comprising a modified alginate, which comprises at least one alginate chain section to which is bonded by covalent bonding at least one molecule useful for cell adhesion and growth, and viable cells for said transplantation.

14. A transplantation matrix comprising a hydrogel of a modified alginate, which comprises at least one alginate chain section to which is bonded by covalent bonding at least one molecule useful for cell adhesion and growth, and viable cells for said transplantation.

15. A method for cell transplantation comprising administering a mixture of a modified alginate, which comprises at least one alginate chain section to which is bonded by covalent bonding at least one molecule useful for cell adhesion and growth, and cells for transplantation.

16. A polymer comprising,
  (a) a polymeric backbone section,
  (b) a side chain comprising polymerized D-mannuronate monomers, L-guluronate monomers or both D-mannuronate and L-guluronate monomers bonded to said backbone, optionally through a linker, and
  (c) a biologically active molecule useful for cell adhesion and growth covalently bonded to the side chain.

17. The polymer of claim 16, wherein the biologically active molecule is bonded through a uronic acid residue on the side chain.

18. The polymer of claim 16, wherein the biologically active molecule is a cell attachment peptide, a peptide growth factor, an enzyme, a proteoglycan or a polysaccharide.

19. The polymer of claim 16, wherein the biologically active molecule is a cell attachment protein.

20. An injectable solution for forming cell transplantation matrices comprising a polymer according to claim 19.

21. An injectable solution of claim 20 further comprising viable cells for said transplantation.

22. A cell transplantation matrix comprising a hydrogel of a polymer according to claim 19 and viable cells for said transplantation.

23. The polymer of claim 16, wherein at least one side chain is bonded through a linker and the linker is a residue of an amino acid, amino aldehyde, amino alcohol, hydrazine, hydrazide or semicarbazide.

24. The polymer of claim 16, wherein the backbone section is a poly(vinyl alcohol), poly(ethylene oxide), polypeptide, poly(amino acid) or poly(uronic acid) polymer section, or modified alginate.

25. The polymer of claim 16, wherein the side chain comprises an oligomeric block unit of D-mannuronate, an oligomeric block unit of L-guluronate, an oligomeric block unit of D-mannuronate and L-guluronate or a mixture of said block units.

26. The polymer of claim 16, having a backbone section with a molecular weight of less than about 50,000.

27. The polymer of claim 26, having side chains each with a molecular weight less than about 50,000.

28. The polymer of claim 16, having a backbone section with a molecular weight above 100,000.

29. The polymer of claim 16, wherein the linker provides a biodegradable bond between the backbone section and the side chain.

30. The polymer of claim 29, wherein the linker is bonded to the polymeric backbone section by an ester group, imine, hydrazone or semicarbazone group.

31. An aqueous composition containing a polymer of claim 16 and water.

32. A polymer comprising,
(a) a polymeric backbone section, and
(b) an alginate side chain, with uronic acid units having carboxylic acid groups, comprising polymerized D-mannuronate monomers, L-guluronate monomers or both D-mannuronate and L-guluronate monomers bonded to said backbone, optionally through a linker, wherein the polymer comprises multiple side chains wherein at least two of said side chains are crosslinked, the crosslinking being with a polyfunctional crosslinking agent having at least two nitrogen-containing functional groups which covalently bond to the carboxylic acid groups in the uronic acid units of the alginate side chains.

33. An alginate material comprising alginate chains with covalently bonded crosslinking between chains, the crosslinking being with a polyfunctional crosslinking agent having at least two nitrogen-containing functional groups which covalently bond to carboxylic acid groups in uronic acid units of the alginate chains.

34. The alginate material of claim 33, wherein the material is crosslinked to the extent such that it resumes essentially its original size and shape after compression.

35. The alginate material of claim 33, wherein the material additionally is gelled by action of a divalent cation.

36. The alginate material of claim 33, wherein the crosslinking agent contains at least two amine, hydrazide or semicarbazide functional groups, or combinations thereof.

37. The alginate material of claim 36, wherein the crosslinking agent is lysine or an alkyl ester thereof.

38. The alginate material of claim 33, wherein 1 mole % or more based on the moles of carboxylic acid groups on uronic acid units in the alginate chains are crosslinked.

39. The alginate material of claim 33, wherein 1–20 mole % or more based on the moles of carboxylic acid groups on uronic acid units in the alginate chains are crosslinked.

40. The alginate material of claim 33, wherein 5–75 mole % or more based on the moles of carboxylic acid groups on uronic acid units in the alginate chains are crosslinked.

41. The alginate material of claim 33, wherein the material is in a viscous liquid form or swellable gel form.

42. The alginate material of claim 33, wherein the material is in a non-swellable, compression resistant form having shape memory properties.

43. The alginate material of claim 33, wherein the material further contains a molecule exhibiting cellular interaction activity bonded to an alginate chain.

44. The alginate material of claim 43, wherein the molecule is a cell adhesion molecule.

45. The alginate material of claim 44, wherein the cell adhesion molecule is a cell attachment peptide, a peptide growth factor, an enzyme, a proteoglycan attachment peptide sequence, a proteoglycan or other polysaccharide exhibiting cell adhesion.

46. The alginate material of claim 43, wherein the molecule exhibiting cellular interaction activity is bonded by covalent bonding to the alginate chain.

47. A matrix for a cell culture system or for tissue engineering composed of the alginate material of claim 33.

48. A method for tissue engineering which comprises introducing as a matrix for the tissue an alginate material of claim 33 in matrix form.

49. The method of claim 48, wherein the alginate material in matrix form is provided before introduction in a suitable size and shape, is altered in size or shape during introducing and essentially resumes its suitable size and shape after introducing.

50. A method for cell transplantation comprising administering a combination of the alginate material of claim 33 and cells for transplantation.

51. A method for treating a human or animal which comprises administering thereto a modified alginate of claim 33, as a matrix for bone or soft tissue replacement.

52. A polymer comprising,
(a) a polymeric backbone section of a poly(vinyl alcohol), poly(ethylene oxide), polypeptide, poly(amino acid) or poly(uronic acid) polymer,
(b) alginate side chains, with uronic acid units having carboxylic acid groups, comprising polymerized D-mannuronate monomers, L-guluronate monomers or both D-mannuronate and L-guluronate monomers bonded to said backbone, optionally through a linker, and
(c) at least one biologically active molecule bonded through a uronic acid unit on an alginate side chain.

53. The polymer of claim 52, wherein the biologically active molecule is a cell attachment protein, a cell attachment peptide, a peptide growth factor, an enzyme, a proteoglycan or a polysaccharide.

* * * * *

UNITED STATES PATENT AND TRADEMARK OFFICE
CERTIFICATE OF CORRECTION

PATENT NO. : 6,642,363 B1
DATED : November 4, 2003
INVENTOR(S) : Mooney et al.

It is certified that error appears in the above-identified patent and that said Letters Patent is hereby corrected as shown below:

Title page,
Item [75], Inventors, "Wai Kung Wong, Laguna" should read -- Wai Hung Wong, Cho Kwo Ling --.

Column 60,
Line 6, "A modified alpinate" should read -- A modified alginate --.
Line 7, "sectiononded" should read -- section bonded --.
Line 15, "a modified alginte" should read -- a modified alginate --.

Signed and Sealed this

Twenty-eighth Day of June, 2005

JON W. DUDAS
*Director of the United States Patent and Trademark Office*